(12) United States Patent
Riester et al.

(10) Patent No.: US 11,662,345 B2
(45) Date of Patent: May 30, 2023

(54) TESTING ASSEMBLY AND TESTING DEVICE FOR LATERAL FLOW ASSAY

(71) Applicant: HOMEDICUS GMBH, Berlin (DE)

(72) Inventors: Markus Riester, Wiesbaden (DE); Michael Diebold, Berlin (DE); Jörn Bungartz, Berlin (DE)

(73) Assignee: HOMEDICUS GMBH, Berlin (DE)

(*) Notice: Subject to any disclaimer, the term of this patent is extended or adjusted under 35 U.S.C. 154(b) by 49 days.

(21) Appl. No.: 16/964,387

(22) PCT Filed: Jan. 23, 2019

(86) PCT No.: PCT/EP2019/051659
§ 371 (c)(1),
(2) Date: Jul. 23, 2020

(87) PCT Pub. No.: WO2019/145374
PCT Pub. Date: Aug. 1, 2019

(65) Prior Publication Data
US 2020/0346209 A1   Nov. 5, 2020

(30) Foreign Application Priority Data
Jan. 24, 2018  (EP) ...................... 18153330

(51) Int. Cl.
*G01N 33/558* (2006.01)
*B01L 3/00* (2006.01)

(52) U.S. Cl.
CPC .......... *B01L 3/5023* (2013.01); *G01N 33/558* (2013.01); *B01L 2300/069* (2013.01);
(Continued)

(58) Field of Classification Search
CPC ............. B01L 3/5023; B01L 2300/069; B01L 2300/0803; B01L 2300/12;
(Continued)

(56) References Cited

U.S. PATENT DOCUMENTS

2002/0173050 A1   11/2002 DiNello et al.
2007/0189928 A1*  8/2007 Sabol ................... A61B 5/1486
                                                        422/68.1
(Continued)

FOREIGN PATENT DOCUMENTS

WO   WO-9010875 A1 *  9/1990
WO   WO 00/65022       11/2000
(Continued)

OTHER PUBLICATIONS

Official Action for European Patent Application No. 18153330.8, dated Apr. 11, 2019, 2 pages.
(Continued)

*Primary Examiner* — Matthew D Krcha
*Assistant Examiner* — Sophia Y Lyle
(74) *Attorney, Agent, or Firm* — Sheridan Ross P.C.

(57) ABSTRACT

A testing assembly for lateral flow assay comprising a liquid sample receiving unit arranged on a support structure defining a plane and configured to receive a liquid sample via the liquid sample receiving interface, at least one testing strip having, in a planar state, a testing strip center line length (L) in a longitudinal direction, a testing strip width in a width direction and a testing strip thickness, and comprising a capillary wick that includes a test portion that comprises a reacting material configured to react in a predetermined manner to a pre-specified analyte, wherein the width direction of the testing strip extends at an angle smaller than 90° with respect to a normal of the plane, and wherein the testing strip is curved, resulting in an effective extension being shorter than the testing strip center line length in the planar state.

26 Claims, 12 Drawing Sheets

(52) U.S. Cl.
CPC ... *B01L 2300/0803* (2013.01); *B01L 2300/12* (2013.01); *B01L 2300/161* (2013.01); *B01L 2300/168* (2013.01); *B01L 2400/0406* (2013.01); *B01L 2400/088* (2013.01)

(58) Field of Classification Search
CPC ......... B01L 2300/161; B01L 2300/168; B01L 2400/0406; B01L 2400/088; G01N 33/558; G01N 33/53
See application file for complete search history.

(56) References Cited

U.S. PATENT DOCUMENTS

| | | | | |
|---|---|---|---|---|
| 2007/0235494 | A1* | 10/2007 | Foran | B65H 35/0073 225/56 |
| 2010/0304986 | A1* | 12/2010 | Chen | B01L 3/502715 435/283.1 |
| 2011/0147244 | A1* | 6/2011 | Chan | G01N 33/48778 29/428 |
| 2014/0302534 | A1* | 10/2014 | Kojima | G01N 33/58 530/387.9 |
| 2015/0004594 | A1 | 1/2015 | Sibbett | |
| 2016/0282343 | A1* | 9/2016 | Jeyendran | G01N 33/558 |

FOREIGN PATENT DOCUMENTS

| | | | |
|---|---|---|---|
| WO | WO 00/77524 | 12/2000 | |
| WO | WO 2006/119203 | 11/2006 | |
| WO | WO-2010017299 A2 * | 2/2010 | ......... A61B 10/0051 |
| WO | WO 2014/072170 | 5/2014 | |
| WO | WO 2016/168490 | 10/2016 | |
| WO | WO 2019/060950 | 4/2019 | |
| WO | WO 2019/067567 | 4/2019 | |

OTHER PUBLICATIONS

Extended Search Report for European Patent Application No. 18153330.8, dated Sep. 6, 2018, 8 pages.

International Search Report and Written Opinion for International (PCT) Patent Application No. PCT/EP2019/051659, dated Feb. 14, 2019, 12 pages.

International Search Report and Written Opinion for International (PCT) Patent Application No. PCT/EP2021/059105, dated Jun. 17, 2021, 13 pages.

International Search Report for International (PCT) Patent Application No. PCT/EP2021/059106, dated Jun. 11, 2021, 10 pages.

* cited by examiner

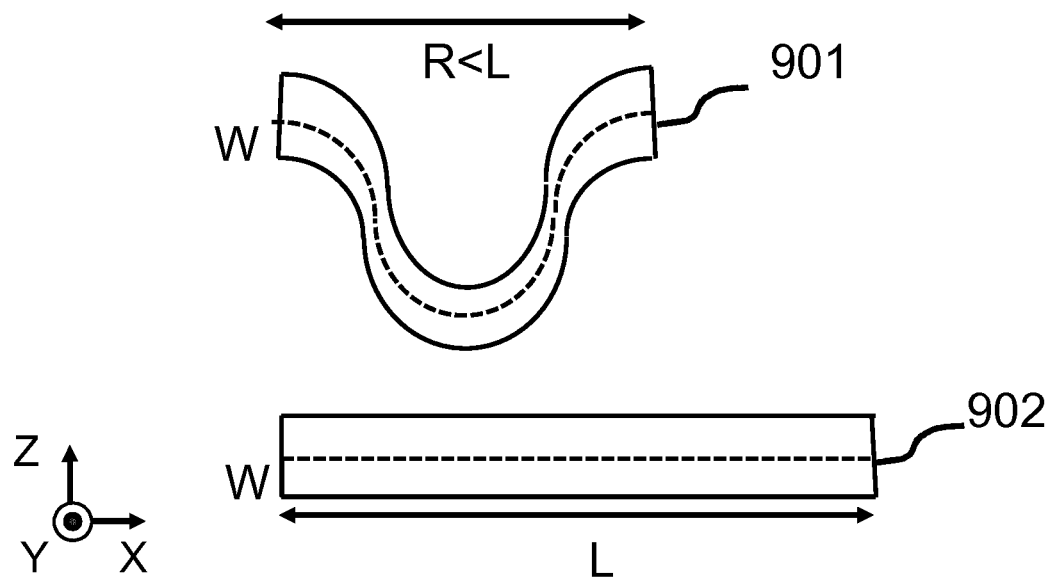
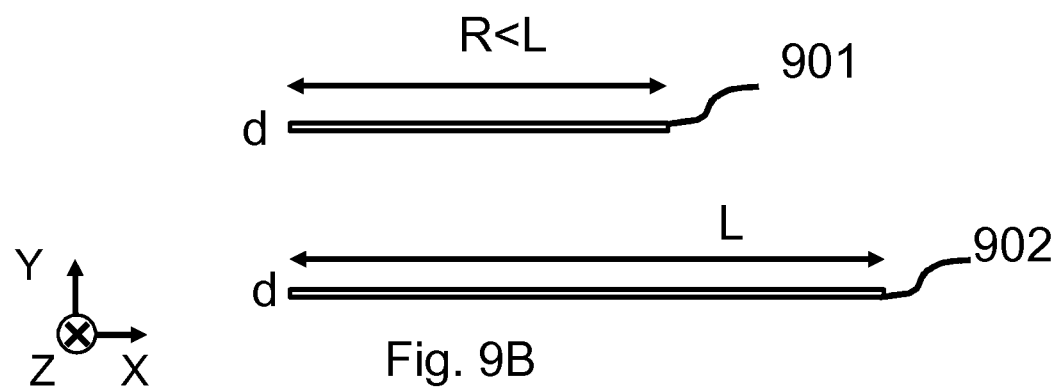
Fig. 9A
Fig. 9B

TESTING ASSEMBLY AND TESTING DEVICE FOR LATERAL FLOW ASSAY

FIELD OF THE INVENTION

The present invention is directed to a testing assembly for lateral flow assay, a testing unit for lateral flow assay and to a testing device for lateral flow assay.

BACKGROUND OF THE INVENTION

Lateral flow assays, also known as lateral flow immunochromatographic assays, are devices intended to detect the presence (or absence) of a target analyte in a sample without the need for specialized and costly equipment. Typically, these tests are used for medical diagnostics either for home testing, point of care testing, or laboratory use. The technology is based on a series of capillary beds having the capacity to transport fluid spontaneously by for example capillarity effect.

US 2015/0004594 A1 describes a semi-quantitative lateral flow assay device and method for generating semi-quantitative data from a lateral flow assay. The device comprises a thin, porous hydrophilic substrate wherein the substrate includes a star-shaped or other geometry taken in a plan view having a liquid sample receiving central region and multiple arms that extend or radiate out from the central region. Each arm includes a reaction zone formed by the presence of an analyte-capturing agent.

SUMMARY OF THE INVENTION

It is an object to provide testing assemblies for lateral flow assay devices that are configured to offer an increased versatility.

The object is achieved by providing a testing assembly for lateral flow assay according to a first aspect of the present invention. This first aspect of the invention mainly relates to the shape and the arrangement of a testing strip of the testing assembly. Further aspects of the invention include a second aspect related to an alternative testing assembly, a third aspect directed to a testing unit comprising a testing assembly of the first aspect or of the second aspect and a fourth aspect directed to a testing device comprising a testing unit of the third aspect of the invention.

The testing assembly of the first aspect of the present invention comprises a liquid sample receiving interface configured to receive a liquid sample. The liquid sample receiving interface is arranged on a support structure that defines a plane. The testing assembly also comprises at least one testing strip that is fluidly connected to the liquid sample receiving interface. The testing strip has, in a planar state, a testing strip center line length, a testing strip width and a testing strip thickness. The testing strip thickness has an extension that is shorter than the testing strip center line length and also shorter than the testing strip width. The testing strip includes a capillary wick fluidly connected to the liquid sample receiving interface and also includes at least one test portion, the test portion of the testing strip comprising at least one respective reacting material configured to react in a predetermined manner to at least one respective pre-specified analyte. The test portion of the testing strip thus acts as a test unit for the liquid sample, where a presence or an absence of a pre-specified analyte is determined.

The testing strip has two flat sides that are spaced apart by the testing strip's thickness. In a planar state, the testing strip has a testing strip length, a testing strip width and a testing strip thickness.

If the testing strip is rectangular (neglecting its thickness) in its planar state, then the testing strip has a testing strip center line length in a longitudinal direction, a testing strip width in a width direction perpendicular to the longitudinal direction and a testing strip thickness in a thickness direction perpendicular to both the longitudinal direction and the width direction, that is shorter, i.e., has a smaller extension, than the testing strip center line length and the testing strip width. In this particular case of a rectangular testing strip, a length of the testing strip and a length of a center line in the middle of the testing strip, hereinafter also referred to as testing strip center line length, is equal to a length of the longitudinal edges of the testing strip's flat surfaces.

Alternatively, the edges of the flat sides may be curved, (i.e. not straight) in the testing strip's planar state. This results in a testing strip having a curved shape in its planar state. In this case the testing strip center line length is the length of a center line located midway between the longitudinal edges of the testing strip. The testing strip center line length is inherent to the testing strip and independent on an actual state—curved or planar—of the testing strip.

The distance between the longitudinal ends of a planar, curved testing strip may be shorter than the length of the center line.

To further limit the outer dimensions of the testing strip—and thus the envelop of the testing strip—the testing strip may be arranged non-planar, i.e. bent or further curved in a third dimension. This includes for example testing strips having straight longitudinal edges that are arranged in a curved state (e.g. rectangular testing strips that are folded, curled or wrapped), testing strips with curved longitudinal edges in a flat state, or testing strips with curved longitudinal edges that are folded curled or wrapped and thus in a curved state).

In the testing assembly of the present invention, a width direction of the testing strip extends at an angle smaller than 90° with respect to a normal of the plane defined by the support structure. i.e. the testing strip extends from the support structure. Also, the testing strip is curved, resulting in a shortest distance between two opposite longitudinal ends of a testing strip center line being shorter than the testing strip center line length in the planar state. The shortest distance is herein defined as a length amount indicative of a minimum distance amount between a proximal end of the testing strip (i.e. a section of the testing strip being in contact with or in the vicinity of the liquid sample receiving unit) and a distal end of the testing strip at which, or close to which, the test portion is arranged.

It is noted that a shortest distance between the longitudinal ends of the testing strip shorter than a center line length implies that the testing strip is curved, either in its planar state, or because the testing strip is arranged non-planar or both. Testing strips wherein the shortest distance between the longitudinal ends is shorter than its center line length have an effective total extension or envelope of the testing strip that is smaller than the testing strip center line length in the planar state. This, in turn, allows for a size reduction of the testing assembly in comparison with a minimum size that the assembly would have in case the testing strips were arranged in the planar state. If the testing strip is curved in a circular shape, the shorter distance between the longitudinal ends may be shorter that the maximum outer dimension of the testing strip while the maximum outer dimension of the testing strip is still smaller than the testing strip center line.

This advantageous spatial arrangement of the testing strips in the testing assembly enables an improved usage of space within the testing assembly. It further enables a reduction of a total size of the testing assembly without a need to reduce the testing strip center line length. This, in turn, results in an improved applicability and offers an increased versatility.

By arranging the testing strips in a curved way and in a way in which the width direction of the testing strip extends at an angle smaller than 90° with respect to the normal of the plane defined by the support structure (i.e. the testing strips not being arranged parallel to the plane defined by the support structure), the size of the testing assembly can be reduced compared to typical testing assembly configurations, wherein the test strips are usually directly arranged on a support structure in the planar state. Alternatively, longer testing strips can be used when compared to known testing assemblies wherein testing strips are arranged in the planar state onto the support structure.

The testing assembly includes a liquid sample receiving interface through which an external liquid sample can be transferred to the one or more testing strips, which are connected in fluid communication thereto. In this way, at least part of the liquid sample can be transferred to the at least one testing strip.

Each testing strip comprises a capillary wick that enables a transport of the liquid sample by capillary action from the liquid sample receiving interface to a respective test portion of the capillary wick. The test portion comprises a reactive material that is configured to react with at least one pre-specified analyte whose presence or absence within the liquid sample is to be tested.

According to a second aspect of the invention, that can be implemented independently from the first aspect, a testing unit is described. An embodiment of the testing unit according to the second aspect of the invention comprises a testing assembly, a cover unit that is attachable to the support structure of the testing assembly and a reflector element.

The testing assembly can be the same as or different from the testing assembly according to the first aspect of the invention. The testing assembly comprises a support structure and at least one testing strip having at least one test portion for outputting a test result. In the testing assembly of the testing unit of the second aspect of the invention, the angle at which a width direction of the testing strip extends with respect to the support structure is not restricted. Also, the testing strip is not necessarily curved, and thus the effective extension is not necessarily shorter than a testing strip center line length in a planar state of the testing strip.

The testing unit of the second aspect comprises a reflector element that is arranged and configured to allow an optical inspection of the test portion of the testing strip from a direction substantially perpendicular to that of the support structure. The reflector element is preferably arranged and configured to guide light from the test portion of the testing strip to an external test-reading device or a user located at a predetermined position outside of the plane based on total internal reflection at an inner surface of the reflector element.

A preferred embodiment of the testing unit of the second aspect additionally comprises a first collimating lens element or a first and a second collimating lens element. The first collimating lens element is arranged between the test portion and the reflector element and the second collimating lens element is arranged between the reflector element and an expected position of the external test-reading device or the user, that is suitable for inspecting the test portion. Preferably, an optical system formed by the reflector element and the first and the second collimating lenses is arranged, within the limits of fabrication, to project an image of the test portion, which is located at a predetermined position, at an infinite distance away from the optical system, or at least to form the image of the test portion at a distance substantially longer than the dimensions of the optical system. In a preferred embodiment of the testing unit of the second aspect, the reflector element is arranged on the cover unit. In an alternative embodiment, the reflector element is arranged on the support structure of the testing assembly.

For an external reading device having a camera lens, the optical axis of the camera lens is preferably arranged co-linearly with that of the second collimating lens. This ensures minimum aberration effects in the formed image.

In an embodiment, the reflecting element comprises a plurality of reflecting surfaces, e.g. a plurality of facets that are configured and arranged to allow for a simultaneous inspection of a plurality of portions of the testing strip. For instance, a testing strip may comprise optical markers such as bar codes or other identification markers that can be simultaneously inspected from outside the testing unit via the reflector element. A reading device can then advantageously obtain an image where the test portion and the identification markers are simultaneously present.

In a preferred embodiment, the testing unit comprises a testing assembly for lateral flow assay. In this particular embodiment, the testing assembly comprises a liquid sample receiving interface arranged on the support structure and configured to receive a liquid sample. The testing strip of this embodiment comprises a capillary wick that is fluidly connected to the liquid sample receiving interface and to the test portion. The testing strip preferably has, in a planar state, a testing strip's center line length, a testing strip width and a testing stripe thickness that is shorter, i.e. has a smaller extension, than the testing strip's center line length and the testing strip width. Such a testing assembly can be combined with any of the technical features described with reference to the different embodiments according to the second aspect.

In a preferred embodiment, the test portion comprises at least one reacting material configured to react in a pre-specified manner to at least one pre-specified analyte.

In another embodiment, each of the testing strips comprise a test portion having a different reacting material configured to react in a pre-specified manner to a respective pre-specified analyte. Alternatively, two or more of the testing strips may one or more test portions having a given reacting material with a same or a respective different sensitivity, in order to either improve the accuracy of testing assembly or in order to enable a semi-quantitative evaluation of the given analyte.

In a preferred embodiment of the second aspect of the invention the width direction of the testing strip extends at an angle smaller than 90° with respect to a normal of a plane defined by the support structure, i.e., the testing strip is inclined with respect to the plane of the support structure, or in other words, the testing strip width is not parallel to the plane. Also, the testing strip is curved, resulting in an effective extension being shorter than the testing strip center line length in the planar state.

An embodiment of testing unit of the second aspect additionally comprises attaching means configured to releasably connect the testing assembly and the cover unit. Suitable attaching means comprise, in a particular embodiment, a bayonet-type attaching structure that comprises at least one peg and a corresponding slot at a respective one of the testing assembly and the cover unit. This feature can be used in combination with any of the embodiments of a testing unit described above.

In another embodiment of the testing unit, the at least one peg is arranged on the testing assembly, particularly on the support structure, and the corresponding slot is arranged on the cover unit. Alternatively, in another embodiment, the at least one peg is arranged on the cover unit and the corresponding slot is arranged on the testing assembly, particularly on the support structure of the testing assembly.

Alternative embodiments comprise other attaching means, such as, but not limited to threading elements, snap-lock elements or lock tabs.

The testing unit of the second aspect of the invention is suitable for connecting one or more of the liquid samples providing modules that will be described below with reference to a fourth aspect of the invention, thus forming a testing device.

In the following, embodiments of the testing assembly of the first aspect and of the second aspect of the invention are described.

In a preferred embodiment of the testing assembly of the first or the second aspect of the invention, the testing strip center line length is longer than the maximum linear extension of the support structure in the plane.

In an embodiment of the testing assembly of the first aspect or of the testing unit of the second aspect of the present invention, the liquid sample receiving interface is a portion of the testing strip configured to receive the liquid sample. In an alternative embodiment, the liquid sample receiving interface is part of a liquid sample receiving unit. The liquid sample receiving unit is arranged on the support structure defining the plane. This liquid sample receiving unit is thus, in this embodiment, a separate unit having a liquid sample receiving interface and being connected to the at least one testing strip.

Preferably, the support structure of the testing assembly of the first aspect or of the testing unit of the second aspect has maximum linear extension in the plane that is shorter than 10 cm and preferably shorter than 5 cm. In a further embodiment, the maximal linear extension in the plane is equal to or shorter than 2.5 cm. Preferably, the support structure comprises a hole with a diameter shorter than 4 mm and configured to provide access to the liquid sample receiving interface and thus to allow introduction of a liquid sample.

In a preferred embodiment of the testing assembly in accordance with this invention, the support structure has a flat or planar geometry that defines the plane. In an alternative embodiment, however, the support structure is not flat, but an outer perimeter of the support structure defines the plane. In yet another alternative embodiment, neither the support structure nor the outer perimeter directly defines a plane and the plane is defined by averaging the spatial position of at least a part of the support structure or of the outer perimeter.

In a particular embodiment of a testing assembly in accordance with the first aspect or with the testing unit of the second aspect of the invention, the liquid sample receiving unit comprises an absorbent material. The absorbent material is configured to be soaked by the liquid sample transferred to the liquid sample receiving unit via the liquid sample receiving interface. The absorbent material is in one embodiment a porous hydrophilic material, preferably comprising cellulose, polyesters, modified polyesters, or a similar material such as a micro-structured or a sintered polymer. This feature can be combined with any of the technical features described hereinabove with regard to the previous embodiments of the first aspect.

In another particular embodiment of a testing assembly in accordance with the first aspect or with the testing unit of the second aspect of the invention, the capillary wick of the testing strip is directly arranged onto the liquid sample receiving interface or in direct contact with the liquid sample receiving unit and the liquid is directly transferred from the latter to the former by means of capillary action. In an alternative embodiment of the testing assembly, the testing strip is not in direct physical contact with the liquid sample receiving interface or with the liquid sample receiving unit, but connected to it through a is a microfluidic connecting system. Either one of these arrangements can be combined with any of technical features described with regard to the previous embodiments of the first aspect of the invention.

Another embodiment of a testing assembly of this invention, in accordance with the first aspect or with the testing unit of the second aspect, comprises a plurality of testing strips. This embodiment may have at least two testing strips arranged spirally so as to have a respective different projection on the plane defined by the support structure. Alternatively, the testing strips may be arranged on each other along a direction perpendicular to the plane defined by the support structure, so that they share a same projection onto the plane. In other words, a total width of the plurality of testing strips arranged on each other corresponds to an addition of each of the testing strip widths of the individual testing strips.

Alternatively, both configurations discussed above are included, i.e. the embodiment of the testing assembly comprises at least two subsets of at least two testing strips, each subset having a different projection onto the plane defined by the support structure the projection shared by all of the testing strips belonging to the subset. Here again, any one of these possible spatial arrangements of the testing strips can be combined with any of the technical features described hereinabove with regard to the previous embodiments of the testing assembly.

In another embodiment of the testing assembly of the first aspect or of the testing unit of the second aspect of the invention, that may further comprise any of the technical features discussed above, the at least one testing strip is advantageously arranged so that an angle formed between the width direction and the plane defined by the support structure at each longitudinal position along the longitudinal direction of the testing strip is constant. Thus, the angle between the width direction of the testing strip and the normal of the plane defined by the support structure is constant for every point along the testing strip center line length. This configuration allows for an optimization of the use of the space within the testing assembly. The angle is, in a particular embodiment smaller than 45°. In a preferred embodiment, the angle is lower than 10°. In a more preferred embodiment the angle is lower than 5°. In an embodiment, the angle is 0°. In the latter case, the testing strip is arranged perpendicular (within the limits of fabrication) to a plane defined by the support structure.

In order to allow an optical inspection of the test portion of the capillary wick from a direction substantially perpendicular to the plane defined by the support structure, a particularly advantageous embodiment of the testing assembly of the first aspect of the invention further comprises a reflector element. The reflector element is configured to allow an optical inspection of the test portion of the testing strip. For instance, in a particularly simple embodiment in accordance with this invention, the reflector element comprises an optical mirror arranged on the support structure and configured to create an optical path between the test portion and an external test-reading device or a user located at a predetermined position outside of the plane. In another embodiment, the reflector element is arranged and configured to guide light from the test portion of the testing strip to the external test-reading device or the user located at a predetermined position outside of the plane, based on total internal reflection at an inner surface of the reflector element. This is achieved by a suitable choice of a geometry and refractive index of the reflector element. A particularly advantageous embodiment additionally comprises a first collimating lens element arranged between the test portion of the testing strip and the reflector element. Another embodiment comprises, in addition to the first collimating lens element, a second collimating lens element arranged between the reflector element and an expected position of the external test-reading device or the user, that is suitable for inspecting the test portion. Here again, any variant of the reflector element can be used in combination with any of the technical features discussed with regard to the previous embodiments.

In order to allow for a correct positioning of the testing assembly, the support structure of any embodiment in accordance with the first or the second aspect of this invention preferably comprises a first window section arranged around the liquid sample receiving unit, the first window section being at least partially transparent in a visible wavelength range and arranged to allow a control of a positioning of the liquid sample receiving unit onto an external surface. The first window section thus allows for an optical inspection of a positioning of the testing assembly in general and the liquid sample receiving unit in particular with respect to a desired goal position in an external surface. In this way, the position of the liquid sample receiving interface or, in another embodiment, of the liquid sample receiving unit, with respect to the desired goal position can be inspected by the user and modified until an optimal position for a liquid sample transfer is reached. Any of the embodiments previously described may also comprise the first window section.

Preferably, the capillary wick of the testing strip of any embodiment of the testing assembly of the first aspect or the second aspect of the invention comprises a porous hydrophilic material, preferably comprising cellulose, polyesters, modified polyesters, or a similar material such as a microstructured or a sintered polymer.

Another embodiment of the testing assembly of the first or the second aspect of the invention is advantageously configured to enable a transfer of the liquid sample from the liquid sample receiving interface or the liquid sample receiving unit to the test portion along the capillary wick so that every point along a transfer front of the liquid sample reaches the test portion at substantially the same time. The transfer front is to be understood as a time-variable position of an interface differentiating a region of the capillary wick containing liquid sample and a region of the capillary wick not containing liquid sample. In cases where a transfer velocity of the liquid sample is assumed to be constant for every point in the transfer front, the capillary wick of this embodiment is advantageously arranged to interface with the liquid sample receiving interface and the test portion at a first interfacing line and a second interfacing line respectively, so that a length amount of every lateral path between any point along the first interfacing line and the second interfacing line is substantially constant. The term substantially constant is to be understood as a constant value within reasonable limits of fabrication and determination and includes, in some embodiments, length deviations of up to 5%.

In another embodiment of the testing assembly of the first or the second aspect of the invention, the testing assembly further includes a conjugate pad that comprises a conjugate material. The conjugate pad is configured to release the conjugate material upon contact with the liquid sample. Additionally, the reacting material of the test portion is configured to react in a predetermined manner to a combination of the conjugate material and the liquid sample. This combination is regarded as the pre-specified analyte. The conjugate pad can be included in any of the embodiments of the testing assembly of the first aspect previously discussed.

In another embodiment of the testing assembly of the first or the second aspect of the invention, the absorbent material of the liquid sample receiving unit acts as a sponge and holds the liquid sample. Once soaked, part of the liquid sample migrates (i.e. is transported by, for instance, capillary action) to the conjugate pad which includes the conjugate material in the form of a so-called conjugate, for example as a dried format of bio-active particles in a salt-sugar matrix configured to guarantee an optimized chemical reaction between a target analyte expected to exist in the liquid sample (e.g., an antigen) and a chemical partner thereof (e.g., antibody). The chemical partner is preferably integrated on the bio-active particle's surface. While the liquid sample dissolves the salt-sugar matrix, it also dissolves the particles. In this way, the target analyte binds to the particles while migrating further through the capillary wick towards the test portion. The test portion of the capillary wick comprises one or more areas (often in the form of stripes) where a reacting material, often in the form of a third molecule is present. By the time the liquid sample-conjugate mix reaches these strips, the target analyte has been bound on the bio active particle from the conjugate pad and the reactive material binds the complex. In reaction thereto, when more and more liquid sample has passed the strips, particles accumulate and the strip changes color. Typically, there are at least two strips in the test portion: a control strip that captures any particle and thereby shows that reaction conditions and technology worked fine, and a second strip that contains a specific capture molecule and only captures those particles onto which an analyte molecule has been immobilized.

Any of the embodiment of the testing assemblies of the first or the second aspect described may additionally comprise an absorbent pad on a distal end of the testing strip opposite to a proximal end of the testing strip whereto the liquid sample receiving interface is connected. The absorbent pad is configured to stop a black flow of the liquid sample. The absorbent pad is thus configured to act as a sink for the liquid sample, maintaining a flow of the liquid over the capillary wick and preventing a flow of the liquid sample back to or towards the liquid sample receiving unit.

Any embodiment of the testing assembly of the first or the second aspect of the invention may further comprise at least one solution chamber containing a respective buffer solution, and flow control means configured to control a transfer of the buffer solution to the liquid sample receiving interface or to at least one testing strip. The at least one solution chamber is preferably arranged on the support structured. In a particular embodiment, the solution chamber is provided as a cavity in the support structure.

Some buffer solutions are advantageously chosen to enhance the transfer of the liquid sample to the test portion. Other buffer solutions comprise a reagent that is configured to react with a particular analyte in a predetermined manner.

In a particular embodiment comprising a plurality of solution chambers, different solutions chambers may contain different buffer solutions, which are individually transferred to the liquid sample receiving unit or to a respective testing strip or to a group of testing strips, in accordance with particular requirements of the testing assembly.

Solution chambers and buffer solutions such as those discussed above can be used in combination with any of the technical features described with respect to the previous embodiments.

In an embodiment of the testing assembly in accordance with the first or the second aspect of the invention, the flow control means is configured to control a transfer of the buffer solution to the liquid sample receiving interface or to the liquid sample receiving unit either before the liquid sample is received via the liquid sample receiving interface, or while the liquid sample is being received via the liquid sample receiving interface, or after the liquid sample has been received via the liquid sample receiving interface, or any combination thereof.

In an embodiment of the testing assembly of the first or the second aspect of the invention, the flow control means may alternatively or additionally be configured to control a transfer of the buffer solution to at least one testing strip either before the liquid sample is transferred from the liquid sample receiving interface or the liquid sample receiving unit to the at least one testing strip, or while the liquid sample is being transferred from the liquid sample receiving interface of the liquid sample receiving unit to the at least one testing strip, or after the liquid sample has been transferred from the liquid sample receiving interface or the liquid sample receiving unit to the at least one testing strip, or any combination thereof.

Transferring the buffer solution to the liquid sample receiving interface or to the liquid sample receiving unit or to the capillary wick before the liquid sample is received or transferred respectively causes a wetting of the capillary wick or the absorbent material that in a particular embodiment enhances an absorption capacity.

Transferring the buffer solution to the liquid sample receiving interface or to the liquid sample receiving unit or to the capillary wick while the liquid sample is being received or transferred increases the volume of the liquid present and the flow velocity of the liquid sample and thus reduces the time needed by the liquid sample to reach the test portion of the testing strip.

Transferring the buffer solution to the liquid sample receiving interface or to the liquid sample receiving unit or to the capillary wick after the liquid sample is received or transferred is advantageously used in particular embodiment to wash away the liquid sample towards the test portion.

Any of the variants regarding the transfer of the buffer solution can be used in combination with any of the technical features discussed with regard to any of the previous embodiments of the testing assembly of the first or the second aspect of the invention.

The flow control means may comprise, in an embodiment in accordance with the first or second aspect of the invention, a soluble material configured to be dissolved in the buffer solution at a predetermined dissolution rate and configured to enable a flow of the buffer solution away from the respective solution chamber after a predetermined time span. In another embodiment, the testing assembly comprises a reservoir containing a soluble material, for instance a pharmacologically inactive substance such as for example lactose monohydrate. This soluble material is configured to be dissolved when in contact with the body fluid. The dissolution of the soluble material is configured to bring in contact a piercing means with the solution chamber. The piercing means is configured to pierce the solution chamber and to allow a controlled flow of the buffer solution out of the solution chamber.

A particular embodiment of a testing assembly in accordance with the first or the second aspect of the invention may further comprise hollow needles or catheters or microfluidic connection systems filled with the soluble material. The hollow needles or catheters are configured to pierce the solution chamber upon operation (e.g. by applying pressure, or by actuating the testing assembly in a predetermined manner). Once the solution chamber is pierced, the buffer solution enters in contact with the soluble material. Thus, by a proper choice of the soluble material, its amount, and the geometry of the flow control means and the solution chamber, a time span expanding between piercing the solution chamber and the buffer solution reaching the testing strip or the liquid sample receiving unit is controlled.

A particular embodiment of the testing assembly of the invention includes a support structure that has a circular shape with a diameter length shorter than 5 cm. In this embodiment the liquid sample receiving interface may be arranged at a central position of the support structure. This embodiment is advantageously configured to enable a highly ordered arrangement of the at least one testing strips and thus to facilitate the fabrication of the testing assembly. This is particularly advantageous in testing assemblies with a plurality of testing strips in a spiral configuration. In an alternative embodiment of a testing assembly, the liquid sample receiving interface is arranged away from the central position of the support structure. This is particularly advantageous in testing assemblies wherein two or more testing strips are arranged on each other along the direction perpendicular to the plane. In this particular arrangement, a total width of the plurality of testing strips corresponds to an addition of the individual testing strip widths of each testing strip. For instance, in an exemplary embodiment of the testing assembly, the support structure has an elliptical shape with the liquid sample receiving interface arranged in a position closer to a vertex than to a center of the ellipse. This embodiment is advantageously configured to include longer testing strips than in the case of a circular support structure with the liquid sample receiving unit arranged at the central position.

According to a third aspect of the present invention, a testing unit for lateral flow assay is presented. The testing unit comprises a testing assembly according to any of the embodiments of the first or the second aspect of the present invention described above and a cover unit that is attachable to the support structure.

The different embodiments of the testing unit in accordance with this invention thus share the advantages of the testing assembly of the first aspect or those of any of its embodiments. Thus, any of the embodiments of a testing assembly described above can be included in a testing unit in accordance with the present invention.

As mentioned herein before with reference to the testing assemblies, in an embodiment thereof, the reflector element is arranged on the support structure. Alternatively, in an embodiment of a testing unit, the reflector element is arranged on the cover unit. The reflector cover is configured to allow an optical inspection of the test portion from a direction substantially perpendicular to the plane.

A cover unit comprising the reflector element can also be combined with a testing assembly according to the second aspect to form a variant of the testing unit that is different from that of the third aspect, and that can be implemented independently therefrom. Preferably, an embodiment of the testing unit has a maximum height in a direction perpendicular to the plane defined by the support structure of the testing assembly that is 66% of the maximal linear extension of the testing assembly in the plane.

An embodiment of a testing unit in accordance with this invention further comprises at least a second window section being at least partially transparent in a visible wavelength range and arranged to allow an optical inspection of the testing unit from outside the testing assembly. In a particular embodiment, the second window section is included in the cover unit. In an embodiment of a testing units wherein the testing assembly comprises a reflector element to allow an optical inspection of the testing unit from a direction substantially perpendicular to the plane, the second window section is arranged so that its projection onto the plane encloses at least a portion of the reflector element. In an alternative embodiment, the testing unit has a peripheral wall with in a direction substantially perpendicular to the plane and the second window section is found in said peripheral wall at peripheral wall positions that enable a direct optical inspection of the testing units. Yet another embodiment comprises a respective second window layer in an upper part of the cover unit and in the peripheral wall.

In a particularly advantageous embodiment of the testing unit of the invention, the second window section is arranged in a recessed region of the cover unit, i.e. a region closer to the support structure than the surrounding portion of the cover unit that is substantially parallel to the support structure, i.e. not the peripheral wall. In this embodiment, the second window section may comprise at least one lens, preferably at least a collimating lens. In an embodiment, the at least one lens is made of glass. In an alternative embodiment, the at least one lens is made of an acrylic compound. Another alternative embodiment may comprise other transparent materials known to the person skilled in the art. In yet another embodiment, the second window section comprises an array of micro lenses.

Any of the variants discussed with respect to the second window layer may be combined with any of the technical features disclosed with regard to the previous embodiments of the testing assembly and the testing unit.

An embodiment of the testing unit wherein the second window section is arranged in a recessed region of the cover unit offers an increased protection of the second window section, by reducing the risk of damaging it, by, for instance, unintended scratching. Further, this embodiment is advantageously configured to be used in combination with a test-reading device comprising a photographic camera such as, for instance, a mobile phone device. In some test-reading devices, the camera protrudes from a backside plane of a housing thereof. By arranging the second window section in a slightly recessed region of the cover unit, the mobile phone can be placed on the cover unit maximizing a contact surface between the back side of the test-reading device and the testing unit, thus reducing the risk of an incorrect relative positioning. In an embodiment of the testing unit of this invention, the cover unit may also comprise a non-slip or anti-skid material configured to increase the friction of the testing unit when in contact with other object such as a test-reading device.

The test-reading device may comprise a processor and a memory unit including a software causing the test-reading device to access the camera, analyze the image and interpret the state of the reacting material of the test portion according to a predetermined analysis template. The software may be configured to provide an output signal that comprises result data pertaining to the state of the reacting material. The output signal can then be directly sent to a user interface or, via a wired or wireless communication link to a centralized data processing center, or both.

In these cases, it is desirable to allow an entrance of light into the testing unit to illuminate the test portion of the testing strip during a reading phase of the state thereof. Since it is possible that the test-reading device blocks light paths from an exterior of the testing unit through the second window section, an embodiment of the testing unit preferably comprises further transparent or translucent sections of the cover unit or of the support structure configured to allow light to penetrate inside the testing unit.

Some particular test-reading devices further comprise a source of light such as a flash unit. Depending on the relative spatial arrangement of the camera and the source of light, light from the source of light can also enter the testing unit through the second window section. However, in order to provide a general solution, independently of a particular type of test-reading device, i.e. whether the test-reading device comprises a source of light or its relative arrangement with respect to the camera, an embodiment of the testing unit may comprise an additional window section at the peripheral wall. Additionally, or alternatively, an embodiment of the testing unit of the invention may further comprises light guiding means to guide the light from the additional window section at the peripheral wall to the test portions. For instance, in a particular embodiment of the testing unit, the peripheral wall serves as a light guide. In another embodiment of the testing unit of the invention, the additional window section may additionally or alternatively comprise a transparent or translucid material, preferably glass or an acrylic compound. In a particular embodiment, the material is mated to enable an even distribution of light.

In an embodiment of a testing assembly in accordance with this invention that may be used in combination with any of the previously described cover units to form an embodiment of a testing unit, the capillary wick of the testing strip is arranged on a testing-strip carrier. The testing-strip carrier is advantageously configured to confine at least a part of the incoming light inside a light-guiding layer of the carrier by internal total refection. In a particular embodiment this is achieved by a proper choice of materials with a suitable respective refractive index or position-dependent refractive index profile. In an alternative embodiment, the testing-strip carrier has inner walls at least partially covered by a reflecting or mirroring layer configured to reflect light. Other light-guiding layers comprise microstructures configured to enhance a transport of the confined light towards the test portion. In another embodiment the testing-strip carriers may also comprise a light output section onto which the test portion of the testing strip is suitably arranged. The light output section is configured to enable confined light to exit the testing-strip carrier. Therefore, these particular testing-strip carriers are suitably configured to allow an illumination of the test portion arranged thereon from its rear part. Advantageously, in a particular embodiment, the capillary wick has a thickness that is thin enough to let at least part of the light impinging on the rear part of the test portion to travel to the front part. The light exiting the testing strip carrier through the light output section and through the test portion is detectable by the test-reading device or by a user. In an embodiment, the capillary wick may be white to further enhance the detection of the exiting light. In yet another embodiment, the reaction of the reacting material with the pre-specified analyte may cause the appearance of a contrast line, dot or any other contrast feature on testing strip at the position of the test portion. The contrast feature thus will absorb at least part of the light coming from the rear part at the position of the test portion. The test-reading device or a user is advantageously configured to detect the contrast feature as a dark mark on the test portion.

In an embodiment of the testing assembly that can form part of a testing unit in accordance with this invention, the testing-strip carrier, in a planar state, is a planar waveguide. Planar waveguides often comprise a transparent film with increased refractive index that acts as a light-guiding layer and that is arranged on a substrate. In other planar waveguides, the transparent film is embedded between two substrate layers.

Alternatively, or additionally, the cover unit of an embodiment of the testing unit may comprise an integrated source of light. In an embodiment, the source of light is fed by an electrical power supply unit, for instance a light emitting diode driven by a battery. In an alternative embodiment, the integrated source of light comprises a photoluminescent material, preferably a phosphorescent material, wherein radiation absorbed by the material is re-emitted at a lower intensity for up to several hours after the original excitation. In yet another embodiment, the testing units may comprise, in addition or as an alternative luminal in a reservoir.

In a particular embodiment of a testing unit in accordance with this invention, the support structure of the testing assembly and the cover unit are attachable. The testing unit comprises attaching means configured to releasably connect the testing assembly and the cover unit. Suitable attaching means comprise, in a particular embodiment, a bayonet-type attaching structure that comprises at least one peg and a corresponding slot at a respective one of the testing assembly and the cover unit. This feature can be used in combination with any of the embodiments of a testing unit described above.

In another embodiment of the testing unit, the at least one peg is arranged on the testing assembly, particularly on the support structure, and the corresponding slot is arranged on the cover unit. Alternatively, in another embodiment, the at least one peg is arranged on the cover unit and the corresponding slot is arranged on the testing assembly, particularly on the support structure of the testing assembly.

Alternative embodiments may comprise other attaching means, such as, but not limited to threading elements, snap-lock elements or lock tabs.

Alternatively, a preferred embodiment of the testing unit comprises a cover unit that is non-releasably connected to the testing assembly. In particular, the cover unit may be non-releasably snap-locked to the testing assembly.

A preferred embodiment of the testing unit has a substantially fitting that of a cylindrical shape, even if the cover unit or the support structure or both the cover unit and the support structure present recessed regions, protruding regions or holes. The bottom base is provided by the support structure and the height is an extension of the cover unit in a direction perpendicular to the support structure. The upper base is also formed by the cover unit. Preferably, the diameter of the base is smaller than 50 mm, more preferably smaller than 30 mm and even more preferably smaller than 25 mm. The height of the testing unit is preferably between 10 and 25 mm, more preferably between 6 and 10 mm.

In a preferred embodiment of a testing unit, the support structure and the cover unit comprise a thermoplastic polymer suitable for injection molding. In a preferred embodiment, the cover unit and the support structure comprise a respective thermoplastic polymer with different properties. Preferably, the thermoplastic polymer comprised by the cover unit is translucent or transparent.

A preferred embodiment of a testing unit comprises a testing strip accommodated onto a portion of an inner perimeter of the cover unit. Preferably, the length of the testing strip in a planar state is equal to or smaller than 10 cm, more preferably smaller than 70 mm. The width of the testing strip is preferably equal to or smaller than 6 mm, and more preferably smaller than 4 mm. The maximum thickness of the testing strip is preferably smaller than 3 mm and more preferably smaller than 2 mm. Typically the maximum thickness of the testing strip is located at the position of the test portion. In embodiments having a conjugate pad, the position of this conjugate pad is also the location of maximum thickness.

Preferably, the testing strip is fixed in place so that it cannot move relative to its designated location.

In an embodiment of the testing unit, an inner volume thereof (i.e. the inner volume delimited by the cover unit and by the support structure) comprises a separating structure that divides the inner volume into two sub-chambers by a separation structure. This separating structure thus defines, in a particular embodiment, a lower chamber and an upper chamber. The lower chamber is delimited by the support structure, a lower portion of the peripheral wall of the cover unit and the separating structure. The upper chamber is delimited by the upper portion of the cover unit and the separating structure. The separating structure comprises at least one opening configured to allow the transport of the liquid sample from the lower chamber to the upper chamber. Preferably, the lower chamber is configured to accommodate a liquid sample providing unit such as, but not limited to, a retractable hollow needle. Additionally, or alternatively, the lower chamber may accommodate the one or more solution chamber comprising the one or more buffer solutions, as well as the microfluidic systems configured to transport the buffer solution to the designated location within the testing assembly. Also preferably, the upper chamber is advantageously configured to accommodate the testing strips. Additionally, the upper chamber may further accommodate the reflector element for allowing the optical inspection of the test portion. Another embodiment of the testing device comprises a separating structure arranged to define more than two sub-chambers.

According to a fourth aspect of the present invention a testing device for lateral flow assay is presented. The testing device comprises a testing unit according to the second aspect of the invention and a liquid sample providing module configured to be connected to the testing unit at the liquid sample receiving interface.

The testing device of the fourth aspect thus shares the advantages of the testing assemblies of the first aspect of the invention and of the testing unit of the second aspect of the invention or of any of its respective embodiments. Therefore, any of the embodiments of a testing assembly or of a testing unit can form part of a testing device when combined with a suitable liquid sample providing module.

The testing device for lateral flow assay has thus a modular nature. An embodiment of a testing unit in accordance with this invention may be advantageously configured to be used in combination with a one or more different liquid sample providing modules. This modular nature allows the use of a plurality of different testing unit in combination with a single liquid sample providing module.

Liquid sample providing modules are in a particular embodiment of a testing device a needle or a needle array configured to be fluidly connected to the liquid sample receiving interface. Alternatively, in another embodiment the liquid sample providing module may be a liquid container which is configured to be fluidly connected to the to the liquid sample receiving interface.

In a particular embodiment of a testing device in accordance with this invention, the liquid sample providing module comprises at least one piercing element having a tip and a base end, wherein the base end is configured to interface with the liquid sample receiving interface. In a particular embodiment the piercing element is a hollow needle having a tip, a base end and a channel linking the tip and the base end in fluid communication, and wherein the base end is configured to interface with the liquid sample receiving interface This embodiment of the testing device is thus advantageously configured to extract the liquid sample from a container or living being using the at least one hollow needle, and to transfer the liquid sample from the container or living being to the testing strip via the liquid sample receiving interface, that is in some cases integrated in a liquid sample receiving unit and in other cases is part of the testing strip.

Alternatively, in another embodiment, the liquid sample providing module is a needle, a catheter, a cannula or a lancet, particularly a blood lancet. Any of these examples of liquid sample providing modules can be used in combination with any of the embodiments of the testing unit described above.

Upon operation of an exemplary testing device, a liquid sample is transported, preferably by, but not restricted to, capillary action from the tip to the base end of the hollow needle via the channel that links them in fluid communication. The liquid sample is transported to the testing strip via the liquid sample receiving interface. Once a predetermined amount of liquid sample has reached the liquid sample receiving interface, the liquid sample enters in contact with the one or more testing strips. The predetermined amount of liquid sample depends on a geometry of the liquid sample receiving interface as well as on its physical characteristics, such as the materials comprised, their porosity, etc. The capillary wick of the testing strip enables a transport of the liquid sample, by capillary action, from the liquid sample receiving interface to the test portion, which includes a reactive material configured to react in a predetermined manner to at least one respective pre-specified analyte, particularly by changing a color of the reactive material when the analyte is in the test portion of the testing strip.

In an embodiment of a testing assembly in accordance with this invention, that can be combined with a cover unit and a liquid sample providing module to form an embodiment of a testing device, the soluble material that is configured to be dissolved when in contact with the body fluid may be alternatively or additionally configured to activate a detaching mechanism. The detaching mechanism, when activated, drives a detaching movement of the liquid sample providing module away from the container or the living being from which the liquid sample is extracted. The soluble material may comprise, in one embodiment, a soluble inorganic salt. In an alternative embodiment, the soluble material may be a composite of a soluble salt and polymers.

The detaching mechanism comprises, in a particular embodiment, a biased spring attached to the liquid sample proving module. The dissolution of the soluble material in contact with the liquid sample releases the biased spring thus allowing it to return to an unstressed state. This drives the detaching movement. In embodiments where the liquid sample providing module comprises a hollow needle, the dissolution of the soluble material drives a detachment movement of the hollow needle that in turn drives the needle out of the container or of the living being, thus enabling an end of a liquid sample extraction.

In another embodiment, the detaching mechanism is integrated in the support structure. For instance, the detaching mechanism in one embodiment is a portion of the support structure to which the liquid sample receiving interface is arranged. This portion of the support structure is configured to be in a biased state when the soluble material is not yet in contact with the liquid sample. When the soluble material is at least partially dissolved, the portion of the support structure that is in a biased state is allowed to return to an unbiased or unstressed state. This drives the detachment movement. A particular embodiment includes a bi-stable snap dome forming part of the detaching mechanism. Another embodiment comprises a snap dome that is configured to have two or more activated states, each activated state being activated upon application of a respective force amount or in a respective predetermined order. In an embodiment, one of the activated states is configured to cause a piercing of the solution chamber where the buffer solution is stored. In another embodiment, piercing of the solution chamber is performed upon activation of other actuators or upon reception of predetermined output signals provided by sensing units arranged inside the testing unit.

In an alternative, the detachment mechanism is configured to be directly operable by a user and its operation is not related to the dissolution of the soluble material. For instance, the detachment mechanism of the present embodiment can be a mono-stable snap dome trigger that is activated by applying a predetermined pressure amount. Upon activation, the mono-stable snap dome trigger adopts an unstable state and is configured to return to the stable state after a predetermined time span that depends on the geometry and the material of the snap dome trigger. This snap-dome trigger is in some embodiments configured to drive a retractable liquid sample providing module (for instance a hollow needle) in an outward movement configured to start the extraction of the body fluid when the snap-dome trigger is operated by the user and in an inward movement that is configured to end the extraction of the body fluid.

In an alternative embodiment, the detaching mechanism is a double push bi-stable actuator. A first push by the user is configured to drive the outward movement of liquid sample providing module (e.g. a hollow needle) and a second push by the user is configured to drive the inward movement of the liquid sample providing module, and thus to terminate the extraction of the body fluid.

It is noted that the presence of a liquid sample providing module is not essential. An embodiment of the testing assembly may comprise the soluble material and the detaching mechanism, wherein the detaching mechanism is connectable to an external liquid sample providing module.

A timing function of an extraction of a liquid sample is in a particular embodiment of the testing device suitably controlled by a kind of the soluble material and its amount and taking into account the nature of the liquid sample. The kind of the soluble material and its amount enables a control of a time span expanding between a starting time at which the liquid sample begins to react with the soluble material and an end time at which the detachment movement occurs.

Additionally, in an embodiment of a testing device in accordance with this invention, the detachment movement of the detaching mechanism further causes a piercing of a container containing the buffer solution. The piercing of the container allows the buffer solution to exit the container. The container is suitably arranged so that the buffer solution, in an exiting movement away from the container, carries the extracted liquid sample together with the dissolved soluble material to the testing strip. Alternatively, or additionally, in another preferred embodiment, the buffer solution is directly provided to the testing strip. Here, the buffer solution is brought in contact with the liquid sample and both travel towards the conjugate pad. In an embodiment, the buffer solution is configured to chemically react with at least one analyte of the liquid sample in a pre-specified manner.

The at least one of testing strip of the testing assembly is advantageously arranged so that a shortest distance between two opposite longitudinal ends of the testing strip center line is shorter than the testing strip center line length in the planar state. The spatial disposition of the testing strip within the device results in a strip having a center line with a center line length that is longer than an effective extension, in any coordinate direction, of the curved testing strip or of the testing strip in a curved state. The center line length is thus a length amount indicative of the testing strip length and thus indicative of a longitudinal extension of the curved testing strip or of the testing strip in a curved state, measured along the center line, and thus takes into account the curvature of the testing strip. The shortest distance is a length amount indicative of a minimum distance amount between a proximal end of the testing strip (i.e. a section of the testing strip being in contact with or in the vicinity of the liquid sample receiving unit, or a section of the testing strip comprising the liquid sample receiving interface) and a distal end of the testing strip at which, or close to which, the test portion is arranged. Thus, providing testing strips with a curved geometry or arranging them in a curved state, or a combination of both, allows from a reduction of a size of the testing device for a given center line length of the testing strip. Preferably, an embodiment of a testing devices according to the third aspect of the invention is arranged to have a maximal extension in any spatial direction shorter than 5 cm.

It shall be understood that the testing assembly of claim 1, the testing unit of claim 11 and the testing device of claim 14 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

FIG. 9A shows a top view of a testing strip having curved longitudinal edges in planar state.

FIG. 9B shows a lateral view of a testing strip having curved longitudinal edges in a planar state.

DETAILED DESCRIPTION OF THE EMBODIMENTS

Figure 1A:
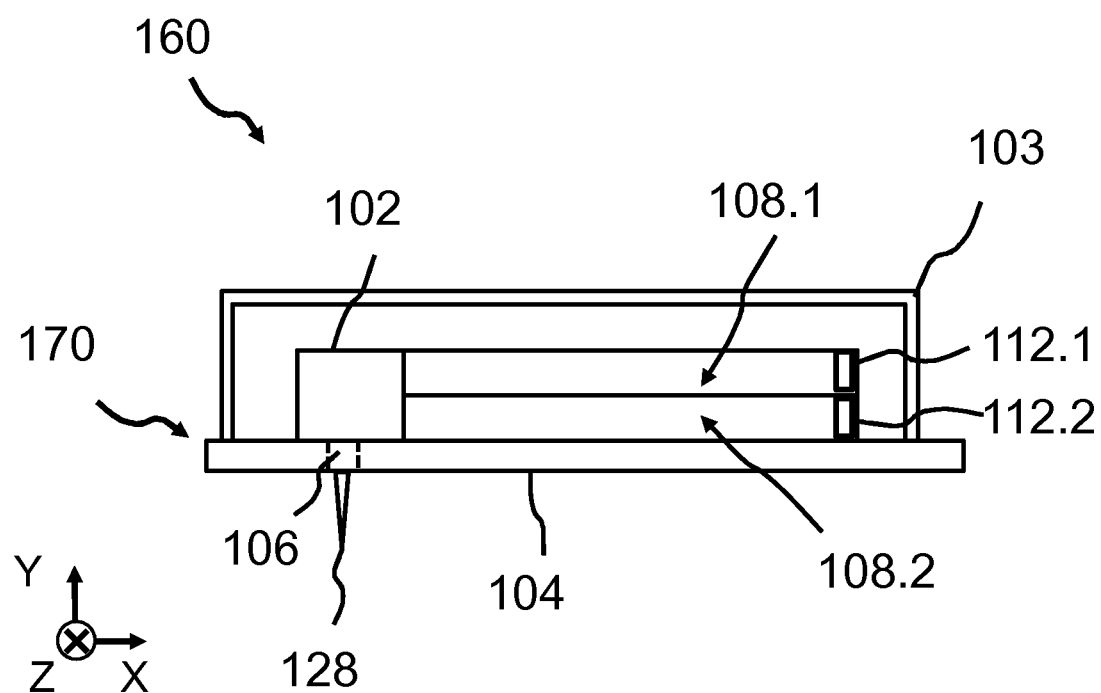
FIG. 1A shows a sectional view of a testing device comprising a needle and a testing unit that includes a testing assembly and a cover unit.

FIG. 1A shows a sectional view of an embodiment of a testing device 160 according to the present invention. The testing device 160 comprises a testing unit and a needle 128. The testing unit includes a testing assembly 170 and a cover unit 103. The needle is a particular and non-limiting example of a liquid sample providing module, and is connected to a liquid sample receiving interface 106 of the testing assembly 170. Other suitable liquid sample providing modules include, but are not limited to, hollow needles, lancets or cannulas The testing assembly further comprises a support structure 104, a liquid sample receiving unit 102 and two testing strips 108.1 and 108.2, each comprising a respective test portion 112.1 and 112.2. These features will be explained in more detail with reference to FIGS. 1B and 1C.

Figure 1B:
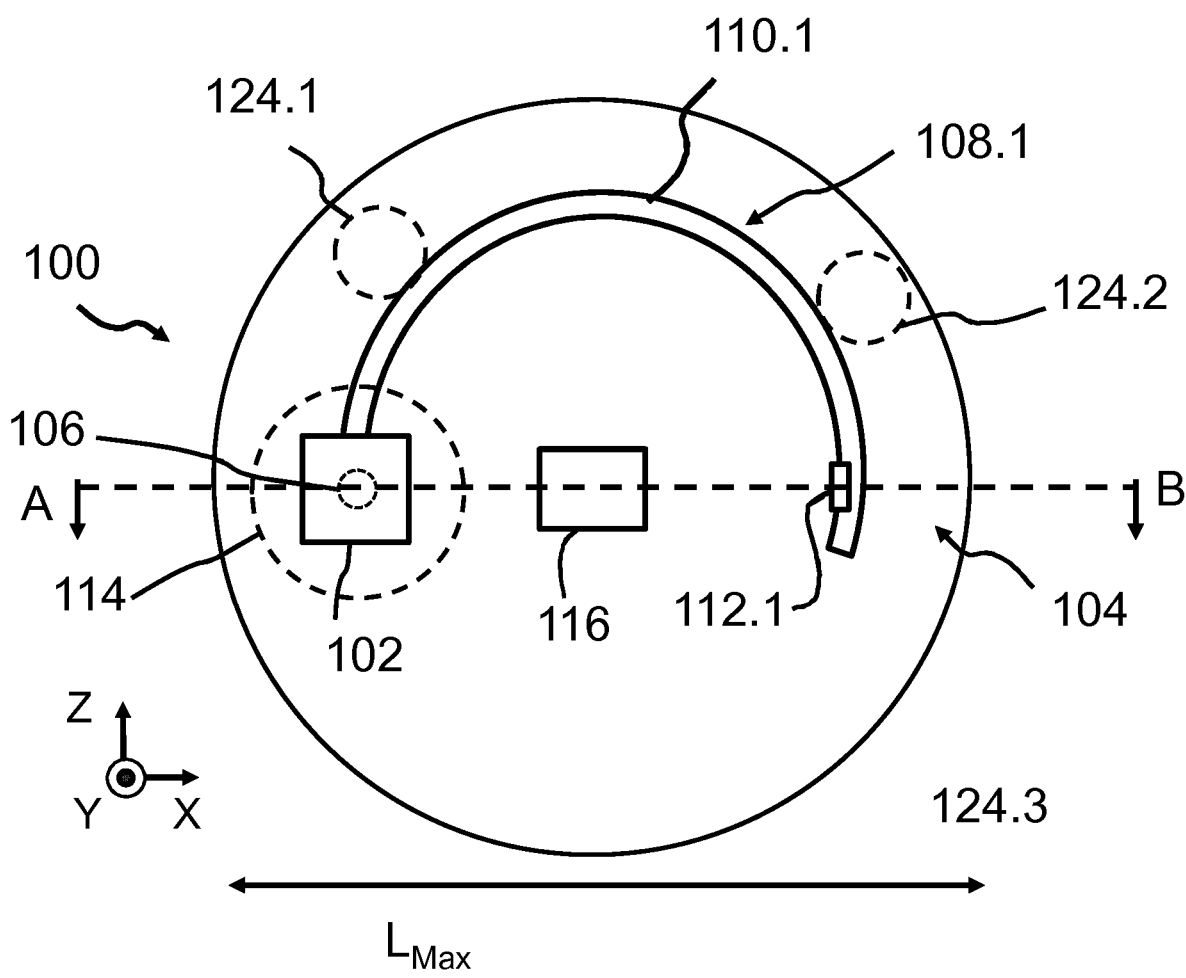
FIG. 1B shows a plan view (top view) of an embodiment of a testing assembly for lateral flow assay.
Figure 1C:
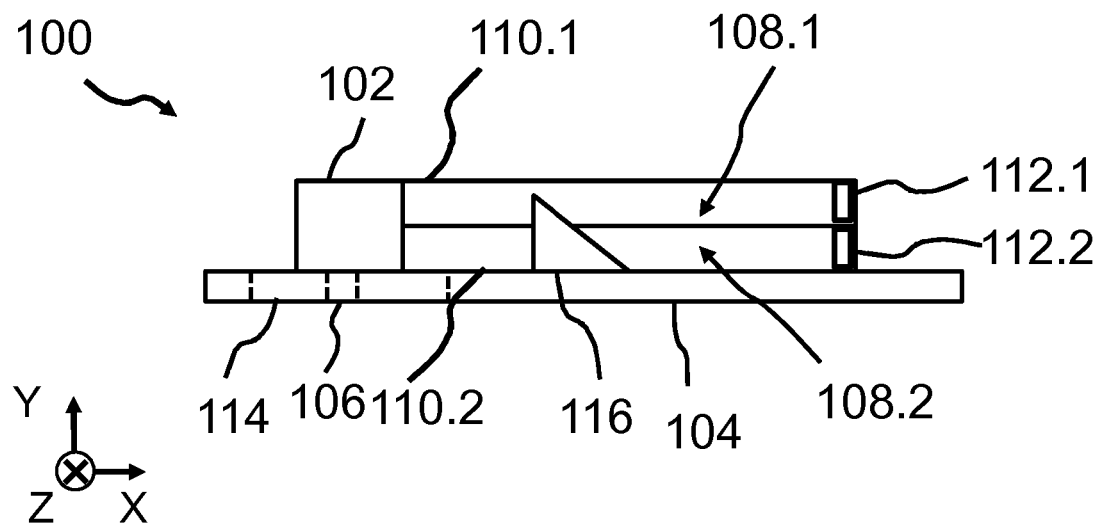
FIG. 1C shows a cross-sectional view of an embodiment of a testing assembly for lateral flow assay.

FIG. 1B shows a cross plan view (top view) of an exemplary embodiment of a testing assembly 100 for lateral flow assay. FIG. 1C shows a cross sectional view across the imaginary line AB of the same exemplary testing assembly 100 for lateral flow assay. FIGS. 1B and 1C, which share the same reference numerals, also with respect to FIG. 1A. The testing assembly 100 comprises a liquid sample receiving unit 102 that is arranged on a support structure 104. In alternative and preferred testing assemblies, the liquid sample receiving unit is arranged on a central position of the support. In other testing assemblies (not shown), the liquid sample receiving interface can be arranged directly on the testing strip, and thus, these alternative testing assemblies do not have a dedicated liquid sample receiving unit, as testing assembly 100 does. The support structure 104 is a flat structure that defines a plane XY as defined by the axes shown in FIGS. 1A, 1B and 1C. The support structure 104 has a largest linear extension $L_{Max}$ that is shorter than 10 cm, and preferably shorter than 5 cm. The liquid sample receiving unit 102 comprises a liquid-sample receiving interface 106 in the form of an opening on the support structure 104, as shown in FIG. 1C. The liquid sample receiving unit 102 is configured to receive a liquid sample via the liquid sample receiving interface 106. The liquid sample receiving unit includes an absorbent material (not shown), preferably a porous hydrophilic material, preferably comprising nitrocellulose or a similar material.

Figure 10:
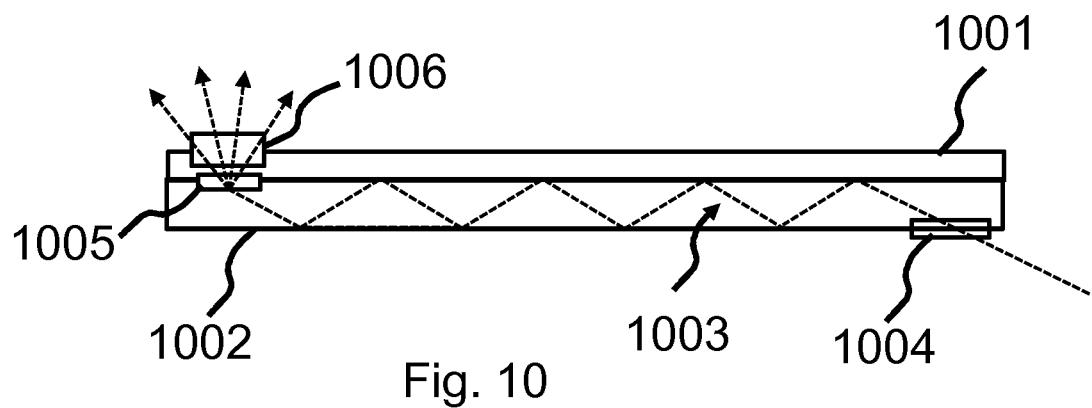
FIG. 10 shows an exemplary arrangement of a testing strip on a testing-strip carrier for enabling an illumination of a test portion of the testing strip.

The testing assembly 100 also includes two testing strips 108.1 and 108.2, as shown in FIG. 10. Each testing strip 108.1, 108.2 is fluidly connected to the liquid sample receiving unit 102 and each comprises a capillary wick (110.1, 110.2) connected to the liquid sample receiving unit 102. Preferably, the capillary wick also comprises a porous hydrophilic material such as nitrocellulose or a similar material. Each testing strip 108.1, 108.2 includes a respective test portion 112.1, 112.2 arranged on the capillary wicks 110.1 and 110.2. The test portions include a respective reacting material (not shown) configured to react in a predetermined manner to at least one respective pre-specified analyte. In some testing assemblies, the test portions 112.1 and 112.2 may contain different reacting materials configured to react to different analytes. In other testing assemblies, the test portions comprise a single reacting material configured to react to a given analyte, with a same or a respective different sensitivity, in order to either improve the accuracy of testing assembly or in order to enable a semi-quantitative evaluation of the given analyte. Other alternative testing assemblies may comprise a plurality of test portions having a given material and additionally at least one test portion having a different reacting material.

In this particular testing assembly 100, the two testing strips 108.1 and 108.2 are arranged so that an angle formed between a width direction of the testing strip (Z, in the particular embodiment of FIGS. 1A, 1B and 1C) and the normal N of the plane (XY) at each longitudinal position along the longitudinal direction of the testing strip is substantially constant with an angle value of substantially 0°, within the practical limits of fabrication and angle determination. This means that the width direction of the testing strip is perpendicular to the support structure 104.

Additionally, a testing assembly in accordance with this invention may further comprise a first window section 114 (dashed line) arranged around the liquid sample receiving unit 102. The first window section 114 is at least partially transparent in a visible wavelength range and is arranged to allow a control of a positioning of the liquid sample receiving unit onto an external surface. By enabling a user to partially see an external surface onto which the testing assembly is to be positioned, the exact position of the liquid sample receiving unit can be advantageously controlled.

The testing assembly 100 also comprises a reflector element 116 configured to allow an optical inspection of the test portion from a direction substantially perpendicular to the plane XY. The reflector element is configured to create an optical path between the test portion and a user or a reading device that is suitably positioned. Alternatively, the reflector element can be arranged on or attached to a cover unit of a testing unit (not shown).

Alternatively, or additionally, some testing devices in accordance with this invention may also comprise one or more solution chambers 124.1, 124.2 (dashed lines) that contain a respective buffer solution. These testing devices also include flow control means (not shown in FIG. 1, see description of FIG. 4) that are advantageously configured to control a transfer of the buffer solution to the testing strips 108.1, 108.2. In some testing assemblies each solution chamber is connected to every testing strip. In alternative testing assemblies, however, some solution chambers are only connected to only one or to a sub-set of the testing strips.

In some testing assemblies in accordance with this invention (not shown), the flow control means may be configured to control a transfer of the solution buffer to the liquid sample receiving interface or to the liquid sample receiving unit. In some testing assemblies comprising two or more solution chambers, at least one of the solution chambers is connected to the liquid sample receiving interface and at least one of the solution chambers is connected at least one of the testing strips.

In any of the previously described testing assemblies, the capillary wick of the testing strip may be arranged on a testing-strip carrier that is configured to confine at least a part of incoming light inside a light-guiding layer of the carrier by total internal reflection achieved, for instance, by a proper choice of materials with a suitable respective refractive index or position-dependent refractive index profile. The testing-strip carriers also comprise a light output section onto which the test portion of the testing strip is suitably arranged. The light output section is configured to enable confined light to exit the testing-strip carrier. Therefore, these particular testing-strip carriers are suitably configured to illuminate the test portion arranged thereon from its rear part. Advantageously, in some embodiments, the capillary wick has a thickness that is thin enough to let at least part of the light impinging on the rear part of the test portion to travel to the front part.

The additional technical features of the testing assemblies discussed above, namely the liquid sample receiving unit 102, the first window section 114, the reflector element 116, the testing-strip carrier and the solution chambers 124.1, 124.3 with the respective flow control means, are not essential features of the testing assembly. However, particularly advantageous testing assemblies many comprise a combination of any subset of them, and, preferably, all of them.

Figure 2A:
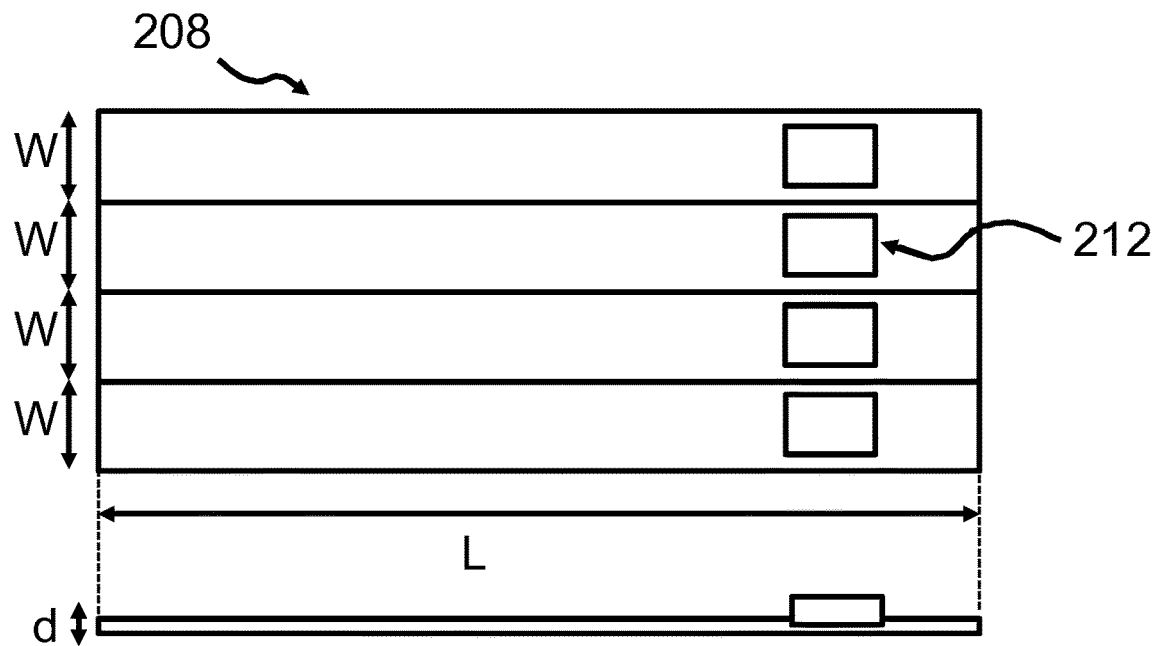
FIG. 2A shows a schematic representation of a top view and a cross sectional view of a set of four testing strips of a testing assembly for lateral flow assay, the testing strips being in a planar state.
Figure 2B:
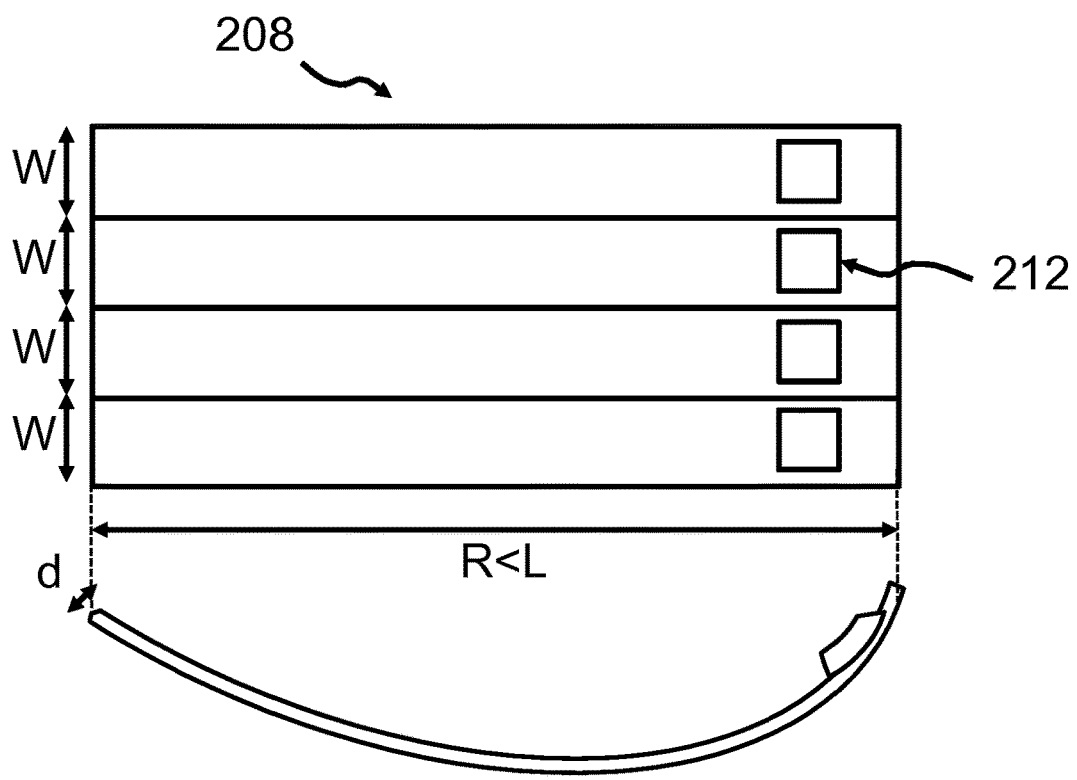
FIG. 2B shows a schematic representation of a top view and a cross sectional view of a set of four testing strips of a testing assembly for lateral flow assay, the testing strips being in a curved state.

The geometry of an exemplary set of testing strips 208 in accordance with this invention is described with reference to FIGS. 2A and 2B. In FIG. 2A, four testing strips form a set of testing strips. Each individual testing strip has a respective test portion 212. Each testing strip is presented in an planar state and has a testing strip center line length L in a longitudinal direction, a testing strip width W in a width direction perpendicular to the longitudinal direction and a testing strip thickness d, in a thickness direction perpendicular to both the longitudinal direction and the width direction, that is shorter, i.e., has a smaller extension than the testing strip center line length L and the testing strip width W. FIG. 2B shows the same set of testing strips 208 in a curved state in which a shortest distance between two opposite longitudinal ends of the testing strip center line, or in other words, an effective extension R is shorter than the testing strip center line length L in the planar state shown in FIG. 2A. In this particular example, the shortest distance between the two opposite longitudinal ends of the testing strip corresponds to the effective extension R. In another exemplary configuration (not shown) wherein the testing strip is bent in e.g. a circular shape, the shortest distance between the two opposite longitudinal ends vanishes, whereas the effective extension corresponds to the diameter of the formed circle, which is π/L. In any case, the shortest distance and the effective extension are shorter than the testing strip center line length.

Other geometries of testing strips that are used in some testing assemblies in accordance with this invention will be described below with reference to FIG. 9.

Figure 3:
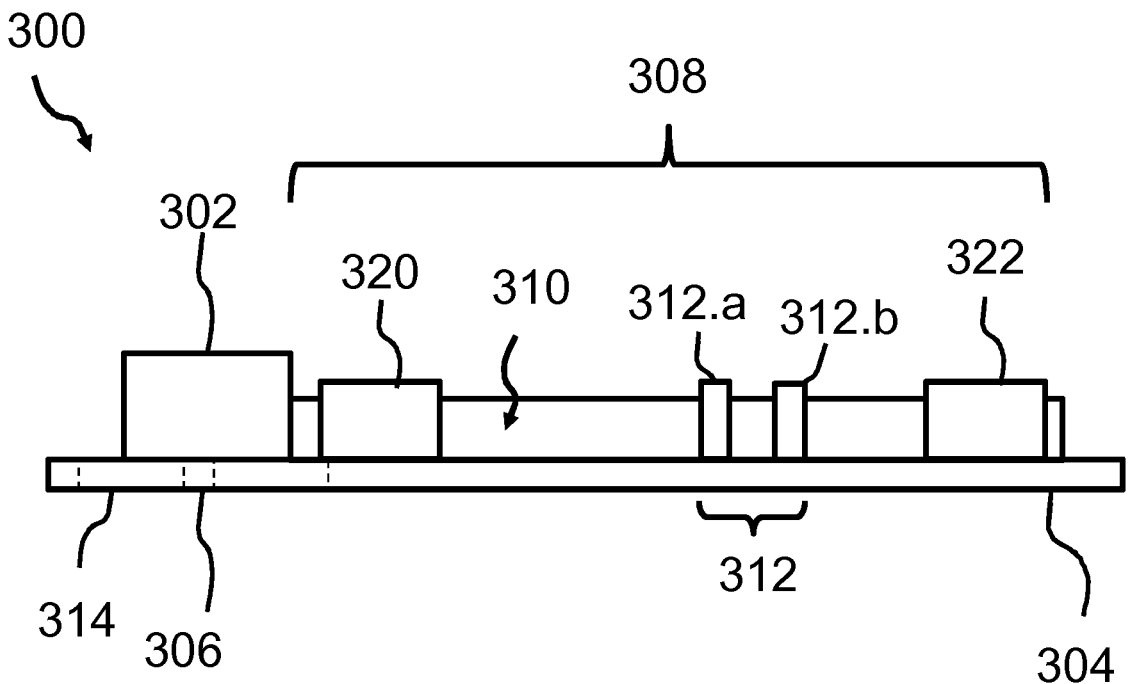
FIG. 3 shows a schematic representation of an embodiment of a testing assembly for lateral flow assay.

FIG. 3 shows a schematic representation of another embodiment of a testing assembly 300. The testing assembly 300 shares many features with the testing assemble 100 described with respect to FIGS. 1B and 1C. Those features shared will be referred to by using the same reference numbers, only altering the first digit, which is "1" when referring to FIG. 1 and "3" when referring to FIG. 3.

The test assembly 300 comprises a support structure 304 that has an opening 306 which, in this particular testing assembly is in connection with a liquid sample receiving unit 302. In alternative testing assemblies, the opening is directly connected to a section of the testing strip acting as a liquid sample receiving interface. The liquid sample receiving interface is advantageously configured to interface with an external liquid sample providing module (not shown). Liquid sample providing modules that can be connected to the liquid sample receiving interface 306 may include, for example, hollow needles or liquid containers with means to transfer a liquid sample contained therein to the liquid sample receiving unit 302 via the liquid sample receiving interface 306. Alternatively, the liquid sample can be directly supplied to the liquid sample receiving interface without the need of a liquid sample providing module. The testing assembly 300 shown in FIG. 3 includes one testing strip 308 in a curved state (nor shown) that is fluidly connected to the liquid sample receiving unit 320. The testing strip 308 comprises a capillary wick 310. The testing strip also includes conjugate pad 320 that comprises an immobilized conjugate material. The conjugate pad 320 is configured to release the immobilized conjugate material upon contact with the liquid sample. The conjugate material is contained in the conjugate pads, i.e. as colloidal gold, or colored, fluorescent or paramagnetic monodisperse latex particles that have been conjugated to one specific biological component expected to be identified in the liquid sample. This biological component is in some testing devices an antigen and in other testing devices an antibody. The testing strip 308 also comprises test portion 312 that includes a test line 312.1 and a control line 312.2 forming a so-called reaction matrix. The liquid sample, received through the liquid sample receiving interface 306 is transported by capillary action from the liquid sample receiving unit 302 along the capillary wick 310. At the conjugated pad 320, the liquid sample releases the conjugate material and a combination of both is further transported towards an absorbent pad 322 located at a distal end of the testing strip 308, opposite to a proximal end whereto the liquid sample receiving unit 302 is connected. The absorbent pad 322 of this (and similar) testing strips is configured to act as a sink for the liquid sample, maintaining a flow of the liquid over the capillary wick and preventing a flow of the liquid sample back to or towards the liquid sample receiving unit 302.

The features distinguishing the testing assembly 300 from testing assembly 100 can be advantageously used in combination with any of the alternatives to the testing device 100 that have been previously discussed. For instance, some testing devices may include, in addition to the features discussed with reference to FIG. 3, a reflector element or at least one solution chamber with respective flow control means, or, preferably, both a reflector element and at least one solution chamber with respective flow control means. Some of these testing assemblies also comprise a testing-strip carrier onto which the capillary wick is arranged.

Figure 4:
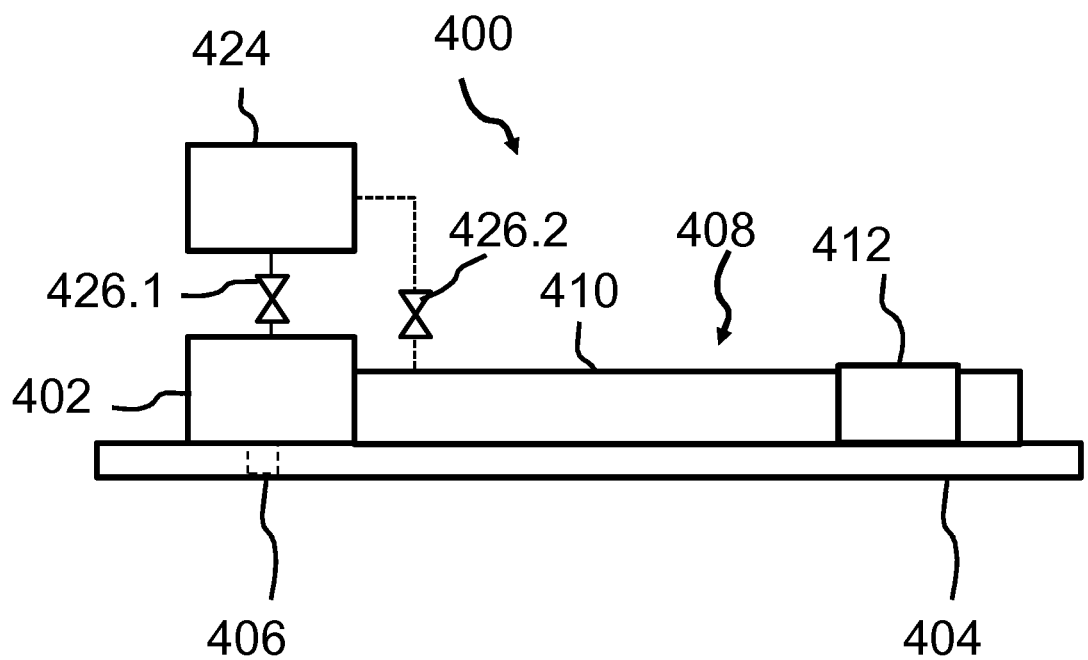
FIG. 4 shows a schematic representation of another embodiment of a testing assembly for lateral flow assay that includes a solution chamber and flow control means.

FIG. 4 shows a schematic representation of another embodiment of a testing assembly 400 that is in accordance with this invention. Here again, the testing assembly 400 shares some features with the testing assemblies 100 and 300 described with respect to FIGS. 1B, 1C and 3. Those features shared are referred to by using the same reference numbers, only altering the first digit, which is "1" when referring to FIG. 1, "3" when referring to FIG. 3 and "4" when referring to FIG. 4. The testing assembly 400 further comprises a solution chamber 424 containing a buffer solution, and flow control means 426.1 configured to control a transfer of the buffer solution to the liquid sample receiving unit 402. Alternatively, or additionally, some testing devices include flow control means 426.2 that control a transfer of the buffer solution directly to the testing strip 408 (as indicated by the dashed-line). Some testing devices include a plurality of solution chambers and control flow means that control a respective transfer of the respective solution (which can be identical or different or a combination thereof) to the liquid sample receiving interface or to one or more testing strips. Buffer solutions are advantageously chosen to enhance a transport of the liquid sample along the capillary wick of the testing strips.

The features distinguishing the testing assembly 400 from testing assemblies 300 and 100 are in some embodiments advantageously used in combination with any of the alternatives to the testing devices 100 and 300 that have been previously discussed. For instance, some testing devices may include, in addition to the features discussed with reference to FIG. 4, a reflector element or at least one solution chamber with respective flow control means, or, preferably, both a reflector element and at least one solution chamber with respective flow control means. Alternatively, or additionally, the testing strip 408 also comprises test portion 412 that includes a test line and a control line forming a so-called reaction matrix.

The capillary wick of some of the testing assemblies in accordance with this invention is advantageously arranged on a testing-strip carrier configured to confine by internal total refection at least a part of incoming light inside a light-guiding layer of the carrier. The test portion of the testing strip is arranged onto a light output section of the testing carrier, so that light confined inside the light-guiding layer can exit it and thereby illuminate the test portion.

Any of the testing assemblies described in the previous discussion can form part of a testing unit in accordance with the second aspect of the present invention. In the following, particular embodiments of testing units of the second aspect will be described with more detail, without intention to thereby restrict the scope of the invention to such cases.

Figure 5A:
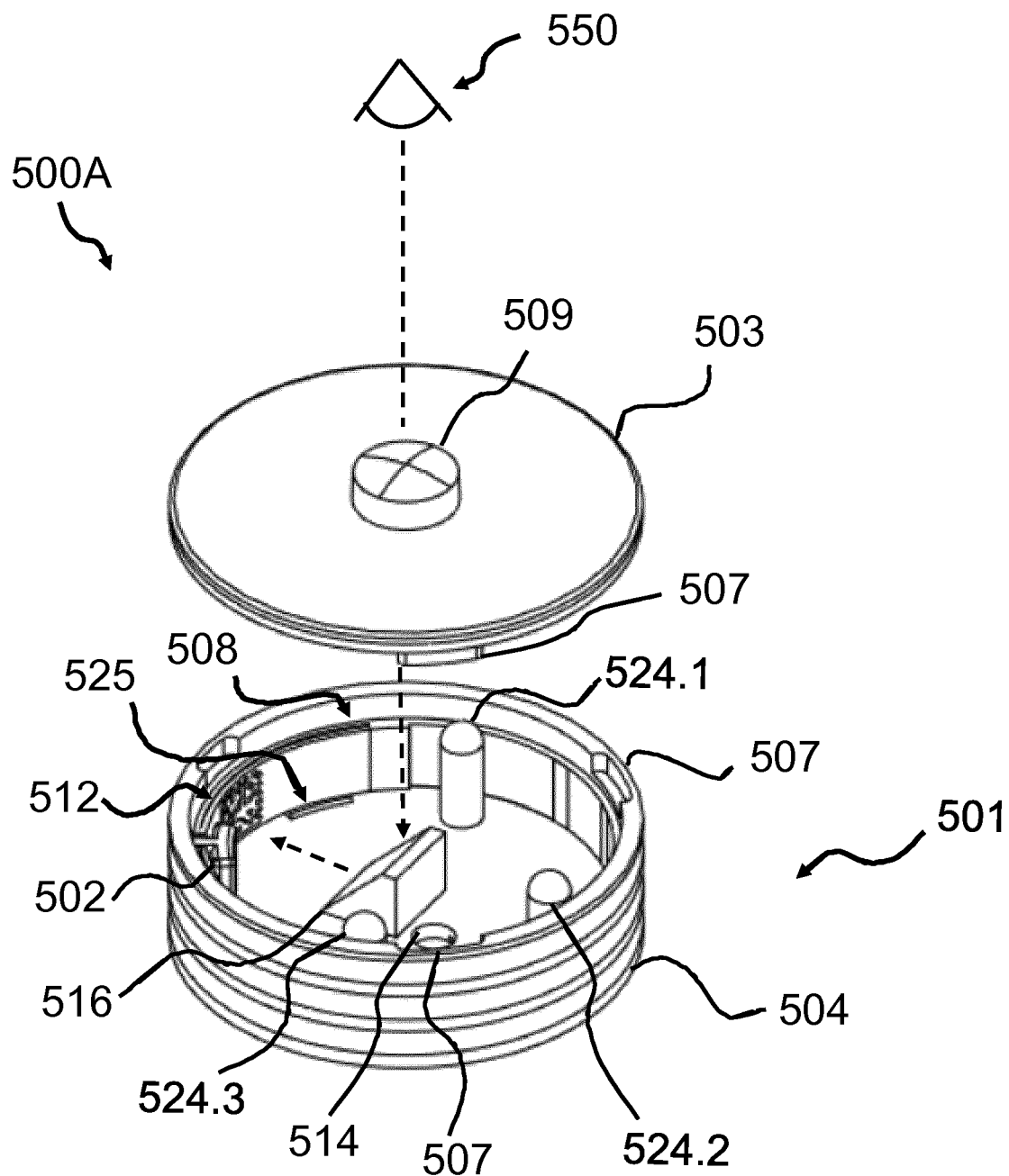
FIG. 5A shows a schematic representation of an embodiment of a testing unit for lateral flow assay comprising a testing assembly and a cover unit, including a reflector element arranged on the support structure
Figure 5B:
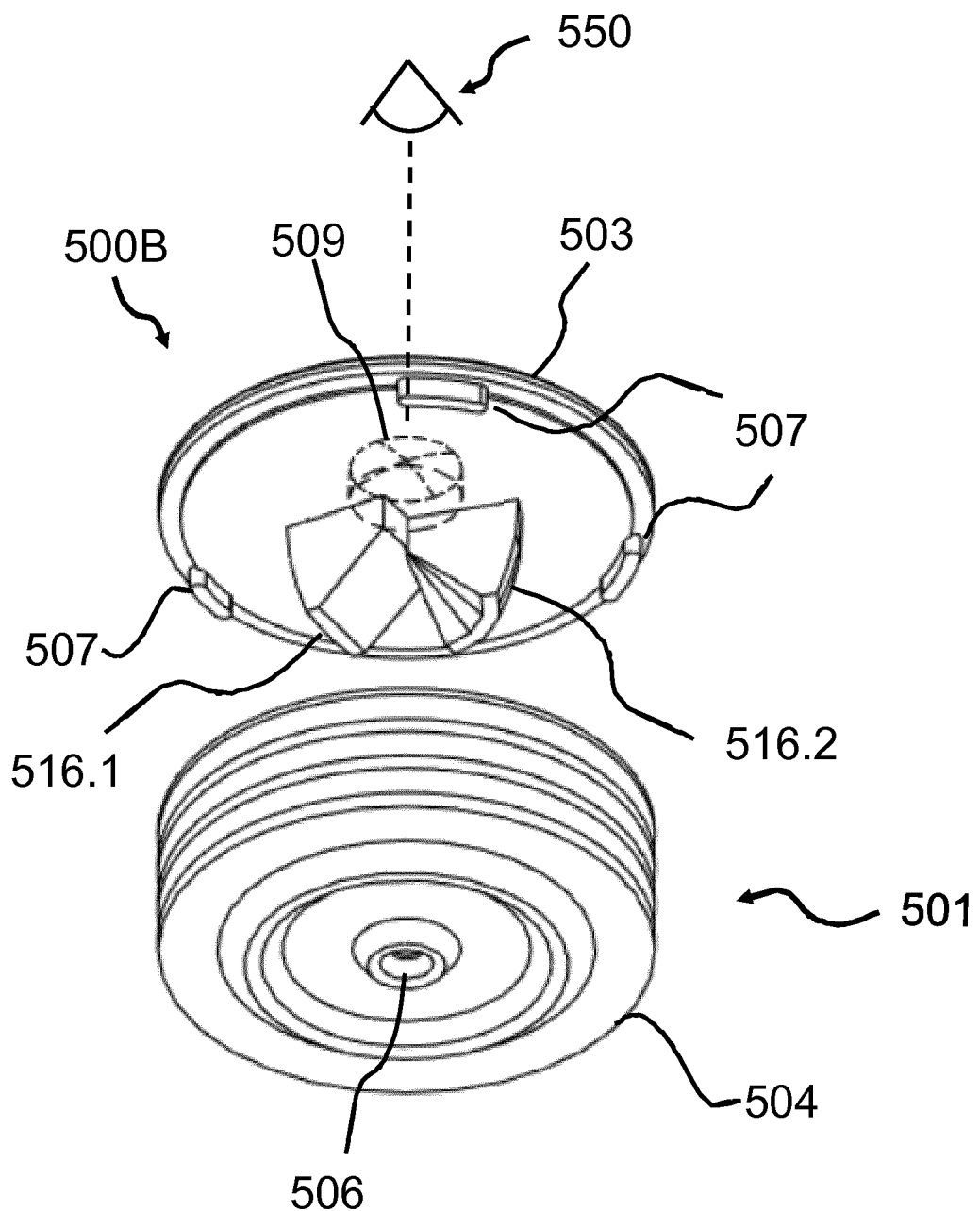
FIG. 5B shows a schematic representation of another embodiment of a testing unit for lateral flow assay comprising a testing assembly and a cover unit, including a reflector element arranged on the cover unit.

FIGS. 5A and 5B show schematic representations of two embodiments of a testing unit for lateral flow assay 500A and 500B. The testing units 500A and 500B comprise a respective testing assembly 501 and a cover unit 503. The testing assembly 501 shares some features with the testing assemblies 100, 300 and 400 described with respect to FIGS. 1B, 1C, 3 and 4. Those features shared are referred to by using the same reference numbers, only altering the first digit, which is "1" when referring to FIG. 1, "3" when referring to FIG. 3, "4" when referring to FIG. 4 and "5" when referring to FIGS. 5A and 5B.

In the particular testing unit 500A, the testing assembly comprises a testing strip 508 and three solution chambers 524.1, 524.2 and 524.3. The testing strip is held in place by means of one or more protruding regions 525 of the support structure. Alternatively, or additionally, the support structure may comprise rails for holding the testing strip in place. The cover unit 503 comprises a second window section 509 that is at least partially transparent in a visible wavelength range and that is arranged to allow an optical inspection of the test portion 512 of the testing assembly 501 from outside the testing unit. The second window section 509 comprises a collimating lens as indicated in FIGS. 5A and 5B by the convex shape of the lens element forming the window section 509. In the exemplary embodiment of FIG. 5A, the testing assembly 501 comprises a reflector element 516 (e.g. in the form of a mirrored surface), arranged on the support structure 504 and configured to enable an optical inspection of the test portions by an external user 550 through the second window section 509, as indicated by the dashed line. Further, the testing units 500A and 500B comprise attaching means to attach the cover unit 503 to the testing assembly 501. In these particular embodiments of the testing unit, the attaching means is configured to releasably connect the testing assembly to the cover unit. The lateral wall of the support structure 504 of the testing assembly 501 comprises a plurality of recessed regions 507. Correspondingly, the cover unit comprises conveniently formed protruding sections 505 (only one is shown in FIG. 5A). The protruding sections 505 are configured to be introduced in the recessed regions 507 to secure the attachment. The recessed regions and the protruding section form a snap-lock element suitable for releasably attaching the cover unit to the testing assembly. Other testing units comprise alternative attaching means such as, but not limited to, pegs and slots, locking tabs, or threading elements.

In the testing unit 500B shown in FIG. 5B, the reflector element is arranged on the cover unit 503. This particular reflector element comprises a first reflecting unit 516.1 and a second reflecting unit 516.2. The first reflecting unit 516.1 is arranged and configured to allow an optical inspection of the test portion of the testing strip from a direction substantially perpendicular to the support structure, as indicated by the dashed line. The second reflecting unit 516.2 comprises a plurality of facets that allow for a further inspection of other portions of the testing strip. For instance, a testing strip comprises optical markers such as bar codes or other identification markers that can be simultaneously inspected from outside the testing unit via the reflector element and through the second window section 509. A reading device can then advantageously obtain an image where the test portion and the identification markers are simultaneously present.

Figure 6A:
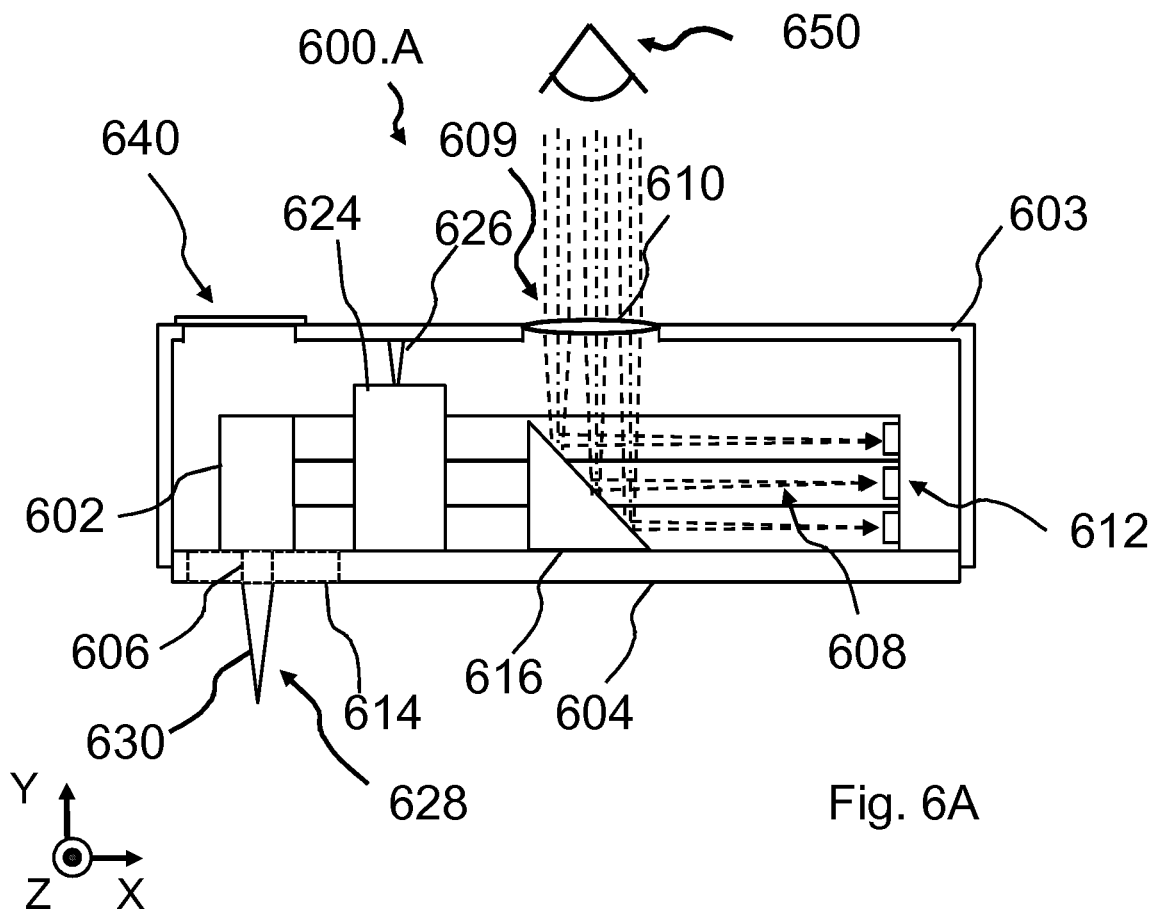
FIG. 6A shows a cross sectional view of an exemplary embodiment of a testing device for lateral flow assay.

FIG. 6A shows a cross sectional view of an exemplary embodiment of a testing device 600.A for lateral flow assay. The testing device 600.A shares some features with the testing unit 500 described with respect to FIG. 5 and with the testing assembly 400 described with respect to FIG. 4. Those features shared are referred to by using the same reference numbers, only altering the first digit, which is "4" when referring to FIG. 4, "5" when referring to FIG. 5 and "6" when referring to FIG. 6A or 6B. The testing device comprises a liquid sample providing module 628 that comprises a hollow needle 630 connected to the liquid sample receiving unit 602 via the liquid sample receiving interface 602. The cover unit comprises a second window section 609 comprising a collimating lens 610 that allows an external user 650 to optically inspect the test portions 612, following an optical path indicated by the dashed lines. The cover unit further comprises a third window section 640 that allows an optical inspection of the first window section 614 and thus allows for a correct positioning of the testing assembly onto an external surface. Additionally, optical markers such as, for instance, bar codes arranged on the testing strip for identification, are suitable for inspection via the third window.

The testing assembly of the testing device comprises a solution chamber 624 and flow control means 626 in the form of a needle configured to pierce the solution chamber and thus enable a controlled flow of the buffer solution. The piercing of the solution chamber can be a result of an external pressure applied to the cover unit 603. The external pressure can also be advantageously used to insert the hollow needle or any other suitable piercing element such as lancets or needles, into a predetermined liquid sample supplier, such as, but not limited to, a container or a vessel of a living being.

Figure 6B:
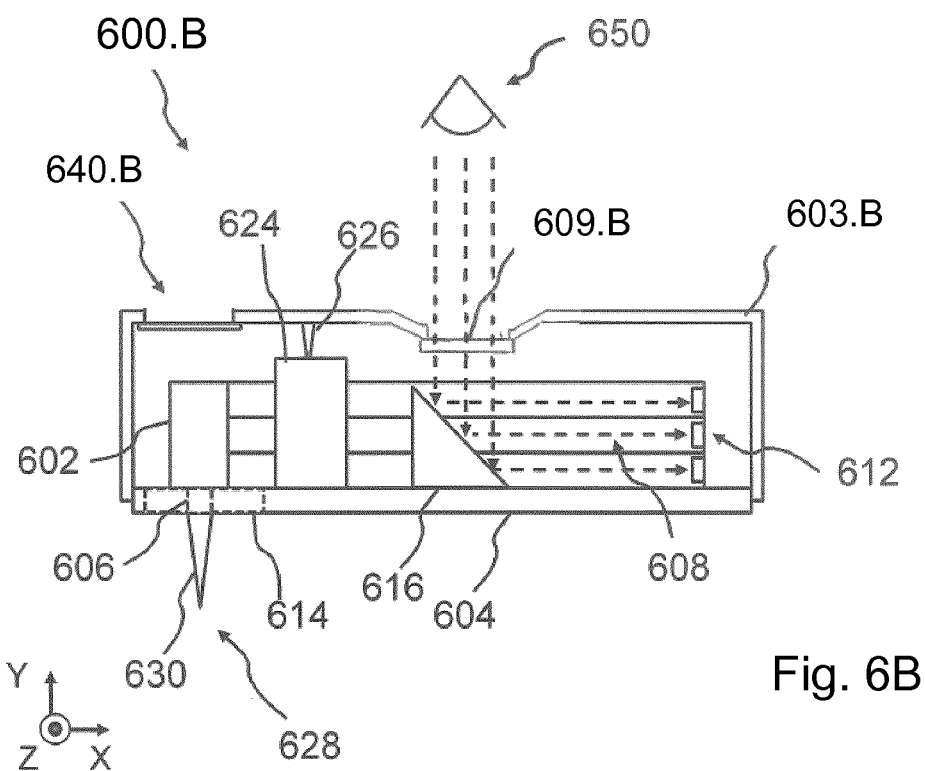
FIG. 6B shows a cross sectional view of another exemplary embodiment of a testing device for lateral flow assay.

FIG. 6B shows a cross sectional view of another exemplary embodiment of a testing device 600.6 for lateral flow assay. The following discussion will focus on the differences between the testing devices 600.A of FIG. 6A and testing device 600.6 of FIG. 6.B. The cover unit 603.6 of testing device 600.6 comprises a recessed region that is closer to the support structure 604 than the surrounding portion of the cover unit (a portion that is parallel to the support structure and not in the peripheral wall). The second window section 609.6 is arranged in this recessed region of the cover unit and may also comprise a collimating lens. This advantageously increases the durability of the second window section which in this configuration is better protected than in the configuration shown in FIG. 6.A or in other configuration wherein the second window section is in-plane with a top region of the cover unit parallel to the support structure. Additionally, in some testing devices the third window section 640.B comprises a transparent layer that is arranged on an inner side of the cover unit.

Figure 6C:
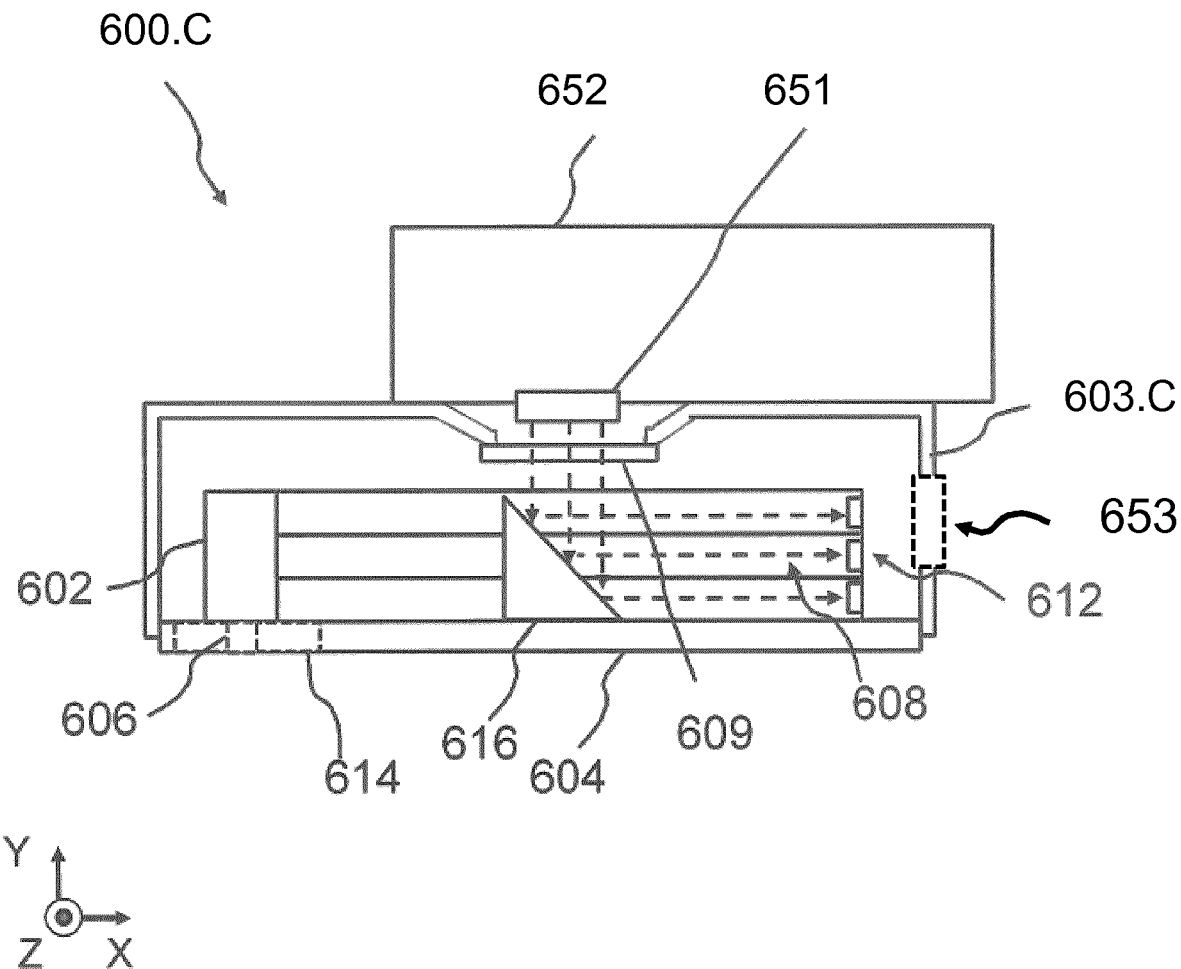
FIG. 6C shows a cross sectional view of an exemplary embodiment of a testing unit for lateral flow assay.

The configuration of the second window section of a testing unit such as the one comprised by the testing device 600.B has further advantages that will be discussed with regard to FIG. 6C, FIG. 6C shows a cross sectional view of an exemplary embodiment of a testing unit for lateral flow assay. The cover unit 603.C of the testing unit 600.C comprises a second window section that is arranged in a recessed region of the cover unit. This configuration is particularly beneficial when used in combination with a photographic camera 651 that is embedded, for instance, in a test-reading device 652. In some test-reading devices the camera 651 protrudes from a back side plane of a housing of the test-reading device. On embodiments of the testing unit, where the second window section is in a same plane as the cover unit, the placement of the test-reading device on the testing unit may be wobbly and a correct positioning of both the testing unit and the test-reading device during a reading phase of the state of the test portion is hard, which may also make the reading of the test portions hard. Providing a recessed second window section mitigates this problem because a protruding camera lens can extend into the recess, thus allowing an easy arrangement of the test-reading device in a parallel, non-oblique and stable manner.

The accuracy of the reading of the state of the test portions of these testing devices can be further enhanced when performed by a test-reading device that is able to obtain a plurality of images, such as for instance by operating in a video-recording mode. An advantageous result-reading software is thus configured to analyze the plurality of images, which, when analyzed alone, may have insufficient resolution for providing an accurate test result. A combined analysis of plurality of images in some cases helps to increase the accuracy of the reading when compared the result obtained by a software configured to analyze a single image. Taking a plurality of pictures with the test reading device may partially compensate for an oblique and instable positioning of the test reading device relative to the testing unit. However, providing means for allowing a stable, parallel arrangement of the test reading device relative to the testing unit is preferred.

In some testing units in accordance with this invention, an outer side of the cover unit, in particular that outer side that is parallel to the support structure 604 may comprise a layer of a non-slip or anti-skid material that increases the friction between the test-reading device and the testing device. This ensures a proper positioning of both devices during a reading phase of the test portions.

Some advantageous testing units in accordance with this invention have cover units and/or support structures that are configured to allow light from outside the testing unit to enter the testing unit and to illuminate the test portion during the reading phase. In some of these testing units, the peripheral wall of the cover unit has one or more additional window sections 653 that allow for an illumination of the test portions. Some testing units also comprise light guiding means to guide the light from the additional window section to the test portions. For instance, some cover units are configured as light guides.

In some of the testing units described above, the testing assembly includes a testing-strip carrier configured to confine at least a part of the light coming through the window section 653 inside a light-guiding layer of the carrier by internal total refection. A light output section of the testing-strip, onto which the test portion is arranged, allows for an illumination of the test portion.

Additionally, or alternatively, some testing units in accordance with this invention comprise an integrated source of light that illuminates the test portion during the reading phase. The light source is in some cases a light emitting diode, driven by an electrical power supply such as a battery. In other cases, the light source comprises a photoluminescent material, preferably a phosphorescent material, wherein radiation absorbed by the material is re-emitted at a lower intensity for up to several hours after the original excitation.

Some of these testing devices may additionally comprise a soluble material that is configured to be dissolved when in contact with the body fluid. The dissolution of the soluble material is configured to activate a detaching mechanism (not shown). The detaching mechanism, when activated, drives a detaching movement of the liquid sample providing module away from the container or the living being from which the liquid sample is extracted. The soluble material comprises in some testing devices a soluble inorganic salt. In other testing devices the soluble material is a composite of a soluble salt and polymers.

The detaching mechanism comprises, in some testing devices in accordance with this invention, a biased spring attached to the liquid sample proving module. The dissolution of the soluble material in contact with the liquid sample releases the biased spring thus allowing it to return to an unstressed state. This drives the detaching movement. In testing devices where the liquid sample providing module comprises a hollow needle, the dissolution of the soluble material drives a detachment movement of the hollow needle that in turn drives the needle out of the container or of the living being, thus enabling an end of a liquid sample extraction.

Figure 7A:
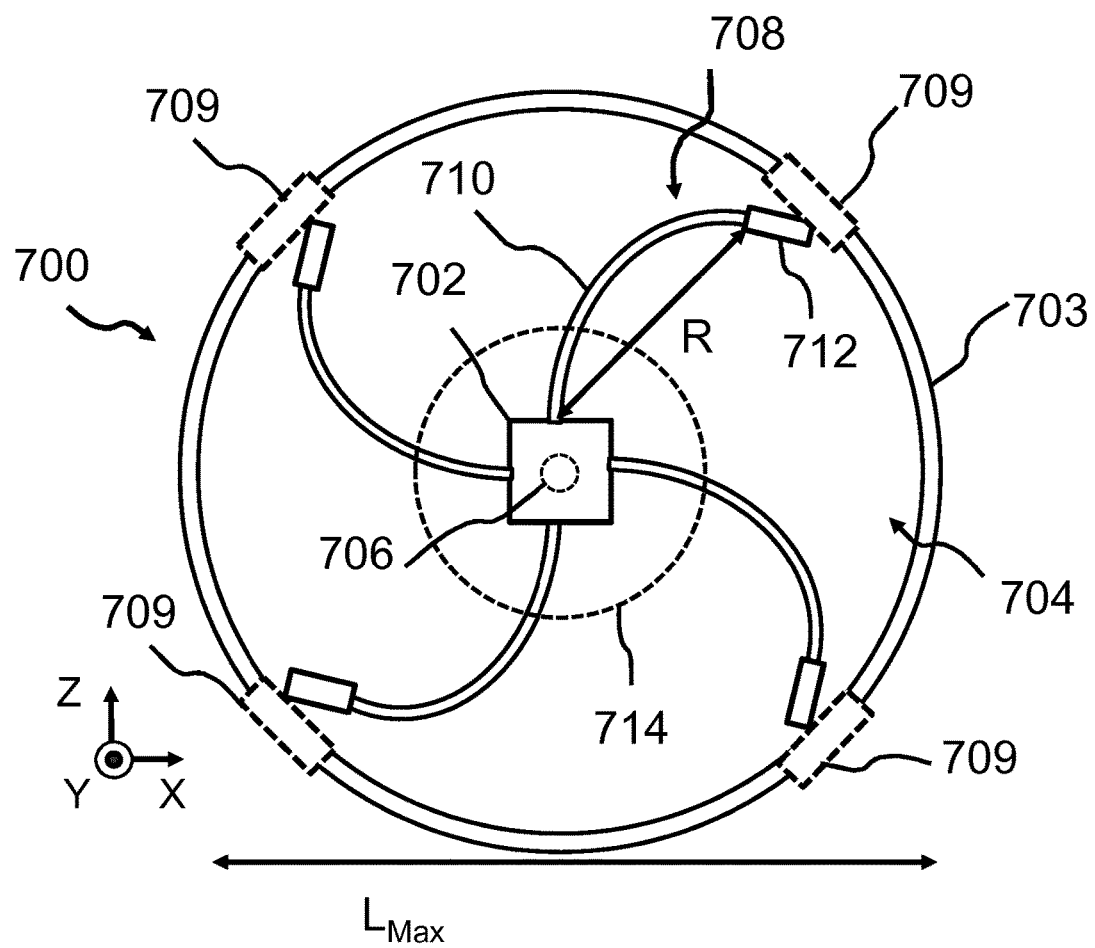
FIG. 7A shows a plan view (top view) of an exemplary embodiment of a testing unit for lateral flow assay.
Figure 7B:
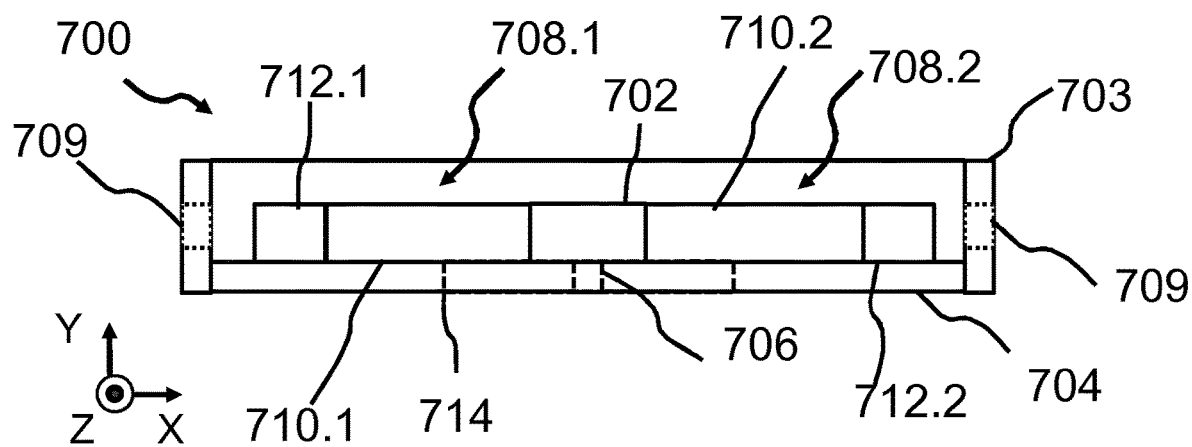
FIG. 7B shows a cross-sectional view of an exemplary embodiment of a testing unit for lateral flow assay.

FIG. 7A shows a planar view (top view) of another exemplary embodiment of a testing unit 700 for lateral flow assay, and FIG. 7B shows a cross-sectional view thereof. Here again, the testing unit 700 shares comprises a testing assembly that shares some features with the testing assembly 100 described with respect to FIG. 1. Those features shared are referred to by using the same reference numbers, only altering the first digit, which is "1" when referring to FIG. 1 and "7" when referring to FIG. 7. In this exemplary testing unit, the support structure 704 is circular with and the liquid sample receiving unit 706 is arranged at a central position of the support structure. The testing assembly comprises four testing strips 708 (708.1, 708.2 in FIG. 7B) that are spirally arranged with a proximal end in contact with the liquid sample receiving unit 706 and a distal end section comprising a respective test portion 712 (712.1, 712.2 in FIG. 7B) which is arranged in a vicinity of a peripheral wall of the cover unit 703. The cover unit comprises four second window sections 709 that are at least partially transparent in a visible wavelength range. The second window sections are arranged to allow an optical inspection of the test portions from an outside region located outside of the testing assembly. Therefore, a user has a direct vision of the test portions for optical inspection of test results (e.g. change in color of the reactive material). In other testing units, the user does not have a direct vision of the test portions but rather an indirect vision thereof, provided by light reflecting means such as mirrors or other reflective surfaces for the given wavelength range.

Figure 8:
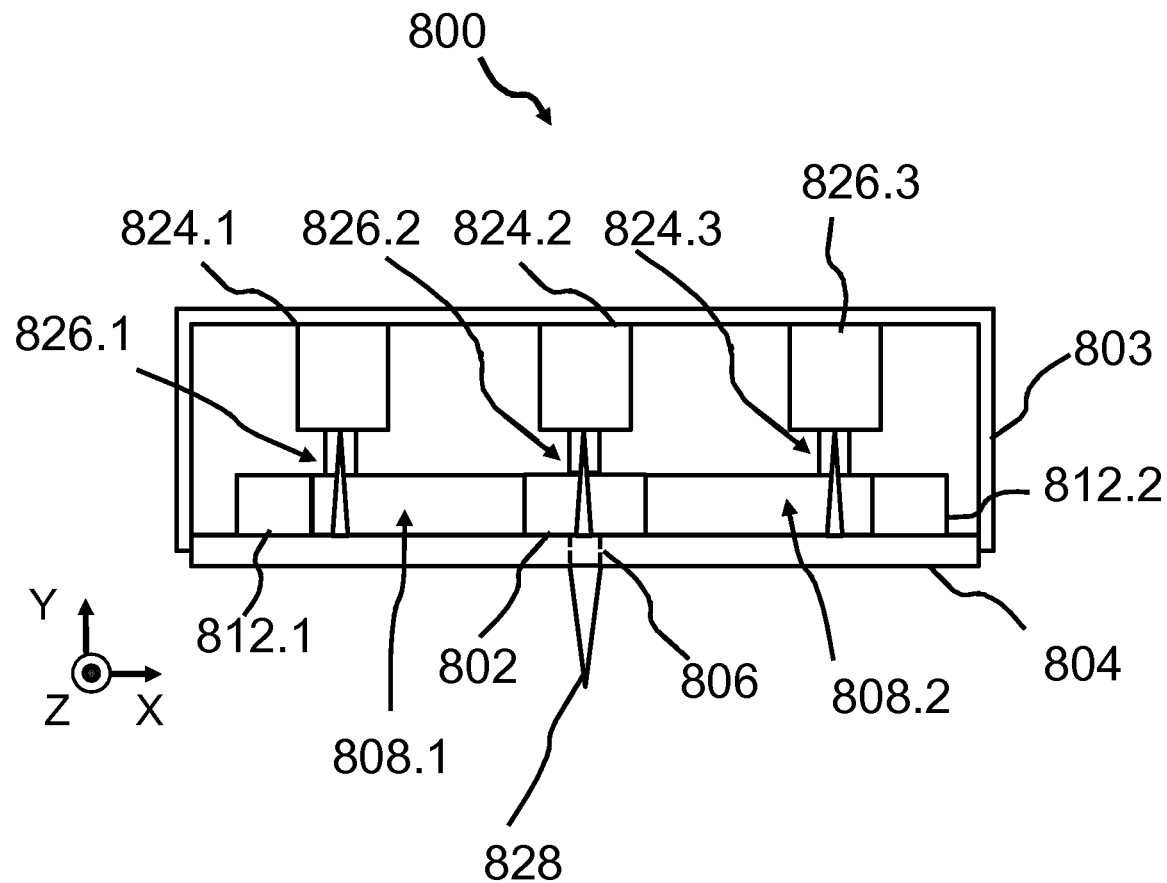
FIG. 8 shows a schematic representation of an embodiment of a testing device.

FIG. 8 shows a schematic representation of an embodiment of a testing device for lateral flow assay. The testing device comprises a liquid sample providing module in the form of a hollow needle 828 that is configured to be connected to the liquid sample receiving interface 806 of the liquid sample receiving unit 802. Here again, the testing device 500 comprises a testing assembly that shares features with the testing assemblies 100 and 400 described with reference to FIGS. 1 and 4. These features share the same reference numbers except for the first digit, which is "1" when referring to FIG. 1, "4" when referring to FIG. 4 and "8" when referring to FIG. 8.

The testing device 800 comprises 3 distinct solution chambers 824.1, 824.2 and 824.3. It also comprises flow control means 826.1, 826.2, 826.3. The flow control means include a hollow needle, configured to puncture the respective solution chamber, and a soluble material (e.g. inside the hollow needle) configured to be dissolved in the buffer solution at a predetermined dissolution rate and configured to enable a flow of the buffer solution away from the respective solution chamber after a predetermined time span. Once pierced, the buffer solution enters in contact with the soluble material inside the hollow needle. Thus, by a proper choice of the soluble material, its amount, and the geometry of the flow control means and the solution chamber, a time span between piercing the solution chamber and the buffer solution reaching the testing strip 810.1, 810.2 or the liquid sample receiving unit 802 can be controlled.

Some testing devices in accordance with this invention include flow control means that are alternatively or additionally configured to control the transfer of the buffer solution while the liquid sample is being transferred to the liquid sample receiving interface via the liquid sample providing module.

Yet other testing devices in accordance with this invention may include flow control means that are alternatively or additionally configured to control the transfer of the buffer solution after the liquid sample has been transferred to the liquid sample receiving interface via the channel of the hollow needle.

FIG. 9A shows a top view of a testing strip in an alternative geometrical configuration that is used in some embodiments of the testing assemblies of the present invention. FIG. 9A shows top views of a testing strip 901 of width W, with curved longitudinal edges and a testing strip center line length L given by the length measure of the center line (dashed lined) and a testing strip 902 with straight longitudinal edges, that has the same width W and the same testing strip center line length L as the testing strip 901). FIG. 9B shows a corresponding lateral view of the testing strips 901 and 902. The thickness of the testing width is given by d.

The testing strip 901 has already in the planar state an effective extension R that is shorter than the maximal longitudinal extension L of the testing strip in the planar state. The effective extension of the testing strip length in the planar state is in the case depicted in FIG. 9 equivalent to the testing strip center line length (dashed line). In order to achieve, for testing strip 902, an effective extension shorter than L, the testing strip 902 has to be arranged in a curved state, e.g. by folding, curving, wrapping, etc. the testing strip 902.

FIG. 10 shows an exemplary arrangement of a testing strip 1001 on a testing-strip carrier 1002. The arrangement is shown in a planar state for the sake of clarity, but it is suitably configured to adopt a curved shape in accordance to the invention. The testing-strip carrier is advantageously configured to confine at least a part of the incoming light (dashed line) inside a light-guiding layer 1003 of the carrier by internal total refection. This is achieved in some testing-strip carriers by a suitable choice of materials with suitable refractive indexes. Other testing-strip carriers have inner walls at least partially covered by a reflecting or mirroring layer configured to reflect light. These testing-strip carriers may additionally comprise a light input portion 1004 to enable an entrance of light into the testing-strip carrier 1002. The testing-strip carrier 1002 also includes a light output section 1005 onto which the test portion 1006 of the testing strip 1001 is arranged. The light output section 1005 is configured to enable confined light to exit the testing-strip carrier 1002 and thereby to allow an illumination of the test portion 1006 arranged thereon from its rear part. For instance, the light output section is in a particularly simple testing-strip carrier a mated portion thereof, where the conditions for total reflection are not fulfilled. Other exemplary light output sections comprise an opening in the testing-strip carrier. This or similar arrangements of a testing strip on a testing-strip carrier can be integrated in any variant of the testing arrangement. For use in a testing unit, care should be taken with respect to the cover unit, since the cover unit should be suitably configured to allow an entrance of light into the testing carrier.

Figures 11A, 11B:
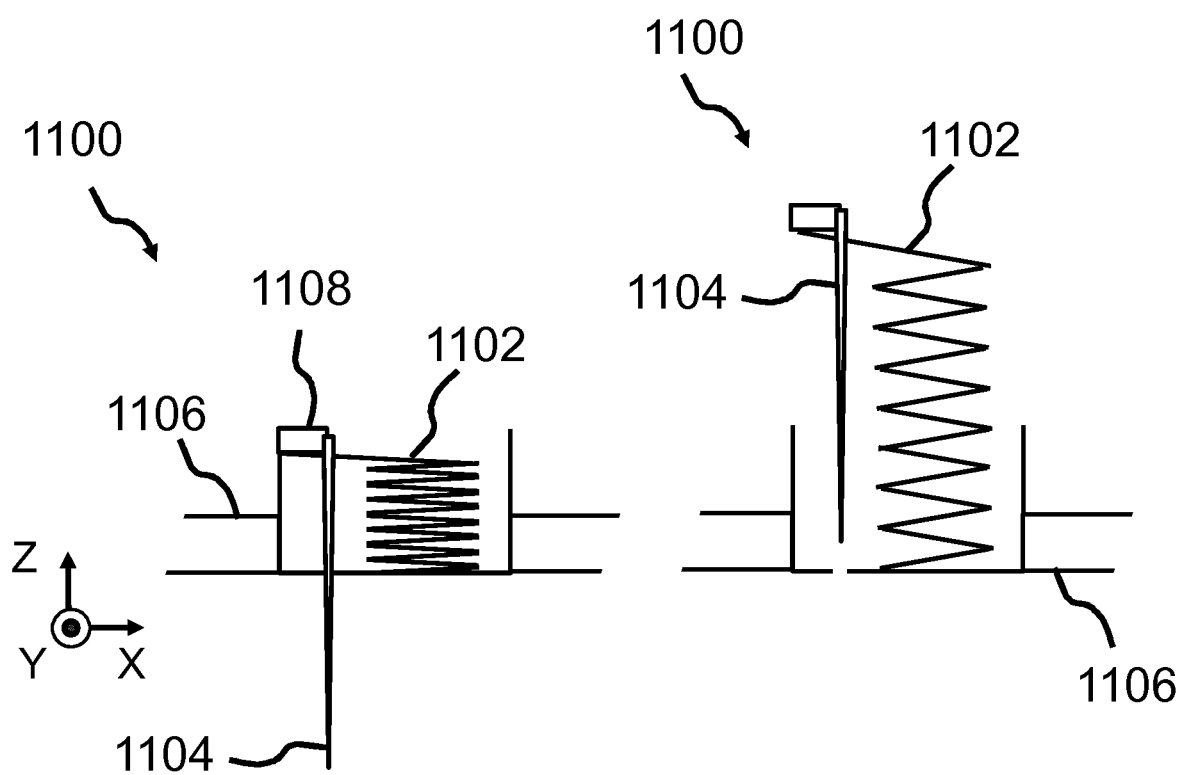
FIG. 11A shows an exemplary detaching mechanism in a biased state.
FIG. 11B shows the detaching mechanism of FIG. 11A in an unstressed state.

FIGS. 11A and 11B show an exemplary detachment mechanism 1100 that may be advantageously used in combination with any of the testing devices described hereinabove. FIG. 11A shows the detaching mechanism 1100 having a spring 1102 in a biased state, wherein FIG. 11B shows the same detaching mechanism 1100 having the spring 1102 in an unstressed or unbiased state. A distal end of the spring 1102 is connected to a hollow needle 1104 that forms in this particular case the liquid sample providing module of the testing device. Other detachment mechanisms in accordance with this invention can be alternatively attached to other liquid sample providing modules such as flexible catheters or other fluidic systems. A proximal end of the spring 1102 is connected to the support structure 1106 of a testing device at an anchor point. The hollow needle 1104 is also in fluid communication with a soluble material 1108 that is configured to remain attached to the support structure as long as a predetermined fraction of the soluble material remains in a solid state. When liquid enters in contact with the soluble material, it causes a dissolution thereof that enables a detachment of the spring 1102 from the support structure 106. The spring is thus allowed to adopt an unbiased state as shown in FIG. 11B, forcing a movement of the needle 1104 in a Z direction. This detachment movement drives the needle from the container or the living being from which it was extracting the liquid sample into an inner volume of the testing device. This detachment movement is configured to end an ongoing liquid sample extraction process. Other detachments mechanisms that can be alternatively used may comprise a bi-stable snap dome, connected to the liquid sample providing unit and wherein a transition from a first stable state to a second stable state is driven by a dissolution of at least a fraction of the soluble material.

In summary, a testing assembly for lateral flow assay in accordance with this invention comprises a liquid sample receiving unit arranged on a support structure defining a plane and configured to receive a liquid sample via the liquid sample receiving interface, at least one testing strip having, in a planar state, a testing strip center line length in a longitudinal direction, a testing strip width in a width direction and a testing strip thickness, and comprising a capillary wick that includes a test portion that comprises a reacting material configured to react in a predetermined manner to a pre-specified analyte, wherein the width direction of the testing strip extends at an angle smaller than 90° with respect to the normal of the plane, and wherein the testing strip is curved, resulting in an effective extension in a curved state being shorter than the testing strip center line length in the planar state.

In the claims, the word "comprising" does not exclude other elements or steps, and the indefinite article "a" or "an" does not exclude a plurality.

A single unit may fulfill the functions of several items recited in the claims. The mere fact that certain measures are recited in mutually different dependent claims does not indicate that a combination of these measures cannot be used to advantage.

The invention claimed is:

1. A testing assembly for lateral flow assay, the testing assembly comprising:
   a support structure defining a plane;
   a liquid sample receiving interface arranged on the support structure, the liquid sample receiving interface being configured to receive a liquid sample;
   at least one testing strip fluidly connected to the liquid sample receiving interface, a testing strip of the at least one testing strip having, in a planar state, a testing strip center line length, a testing strip width and a testing strip thickness that is shorter than the testing strip center line length and the testing strip width, the testing strip comprising:
      a capillary wick fluidly connected to the liquid sample receiving interface by a microfluidic connecting system and including a test portion, the test portion comprising a respective reacting material configured to react in a predetermined manner to at least one respective pre-specified analyte;
   wherein a width direction of the testing strip extends at an angle smaller than 90° with respect to a normal of the plane defined by the support structure; and
   wherein the testing strip is curved, resulting in a shortest distance between two opposite longitudinal ends of a testing strip center line being shorter than the testing strip center line length in the planar state.

2. The testing assembly of claim 1, wherein the testing strip is arranged so that an angle formed between the width direction and the normal to the plane at each position along the testing strip center line length is constant.

3. The testing assembly of claim 1, wherein the support structure comprises a first window section arranged around the liquid sample receiving interface, the first window section being at least partially transparent in a visible wavelength range and arranged to allow a control of a positioning of the liquid sample receiving interface onto an external surface.

4. The testing assembly of claim 1, wherein the capillary wick comprises a porous hydrophilic material comprising cellulose, polyesters, modified polyesters, a micro-structured polymer or a sintered polymer.

5. The testing assembly of claim 1, wherein the testing strip further comprises a conjugate pad comprising a conjugate material and configured to release the conjugate material upon contact with the liquid sample, and wherein the reacting material of the test portion is configured to react in a predetermined manner to a combination of the conjugate material and the liquid sample, such combination being the pre-specified analyte.

6. The testing assembly of claim 5, wherein the testing strip further comprises an absorbent pad on a distal end of the testing strip opposite to a proximal end of the testing strip whereto the liquid sample receiving interface is connected, the absorbent pad being configured to stop a black flow of the liquid sample.

7. The testing assembly of claim 1, further comprising:
a solution chamber containing a buffer solution; and
a flow control means configured to control a transfer of the buffer solution to the liquid sample receiving interface or to the testing strip.

8. The testing assembly of claim 7, wherein the flow control means is configured to control a transfer of the buffer solution from the solution chamber to the liquid sample receiving interface either:
before the liquid sample is received via the liquid sample receiving interface; or
while the liquid sample is being received via the liquid sample receiving interface; or
after the liquid sample has been received via the liquid sample receiving interface; or
any combination thereof.

9. The testing assembly of claim 7, wherein the flow control means is configured to control a transfer of the buffer solution from the solution chamber to the testing strip either:
before the liquid sample is transferred from the liquid sample receiving interface to the testing strip; or
while the liquid sample is being transferred from the liquid sample receiving interface to the testing strip; or
after the liquid sample has been transferred from the liquid sample receiving interface to the testing strip; or
any combination thereof.

10. A testing unit for lateral flow assay, the testing unit comprising:
the testing assembly according to claim 1; and
a cover unit attachable to the support structure.

11. The testing unit of claim 10, further comprising at least a second window section being at least partially transparent in a visible wavelength range and arranged to allow an optical inspection of the test portion from outside the testing unit.

12. The testing unit of claim 10, wherein the testing assembly is non-releasably connected to the cover unit.

13. The testing unit of claim 10, further comprising a reflector element arranged on the cover unit and configured to allow an optical inspection of the test portion from a direction substantially perpendicular to the plane.

14. A testing device for lateral flow assay, the testing device comprising:
the testing unit according to claim 10;
a liquid sample providing module configured to be connected to the testing unit at the liquid sample receiving interface.

15. The testing device of claim 14, wherein the liquid sample providing module comprises at least one piercing element or a cannula having a tip and a base end, wherein the tip protrudes outwardly from the support structure and wherein the base end is configured to interface with the liquid sample receiving interface.

16. The testing assembly of claim 1, wherein the support structure comprises a hole with a diameter shorter than 4 mm and configured to provide access to the liquid sample receiving interface and thus to allow introduction of the liquid sample.

17. The testing assembly of claim 1, wherein the at least one testing strip is a plurality of testing strips, each testing strip being fluidly connected to the liquid sample receiving interface.

18. The testing unit of claim 10, wherein the testing strip is fully enclosed within the support structure and the cover unit.

19. The testing unit of claim 10, wherein the at least one testing strip is a plurality of testing strips, each testing strip being fluidly connected to the liquid sample receiving interface.

20. A testing unit for lateral flow assay, the testing unit comprising:
a testing assembly comprising:
a support structure defining a plane;
a liquid sample receiving interface arranged on the support structure, the liquid sample receiving interface being configured to receive a liquid sample;
at least one testing strip fluidly connected to the liquid sample receiving interface, a testing strip of the at least one testing strip having, in a planar state, a testing strip center line length, a testing strip width and a testing strip thickness that is shorter than the testing strip center line length and the testing strip width, the testing strip comprising:
a capillary wick fluidly connected to the liquid sample receiving interface by a microfluidic connecting system and including a test portion, the test portion comprising a respective reacting material configured to react in a predetermined manner to at least one respective pre-specified analyte;
wherein a width direction of the testing strip extends at an angle smaller than 90° with respect to a normal of the plane defined by the support structure;
wherein the testing strip is curved, resulting in a shortest distance between two opposite longitudinal ends of a testing strip center line being shorter than the testing strip center line length in the planar state;
a cover unit attachable to the support structure; and
a reflector element arranged on the cover unit and configured to allow an optical inspection of the test portion from a direction substantially perpendicular to the plane.

21. The testing unit of claim 20, wherein the testing strip is fully enclosed within the support structure and the cover unit.

22. The testing unit of claim 20, wherein the at least one testing strip is a plurality of testing strips, each testing strip being fluidly connected to the liquid sample receiving interface.

23. A testing device for lateral flow assay, the testing device comprising:
 a testing unit for lateral flow assay; and
 a liquid sample providing module configured to be connected to the testing unit, the testing unit comprising:
  a testing assembly for lateral flow assay; and
  a cover unit attachable to a support structure, the testing assembly comprising:
   a liquid sample receiving interface arranged on the support structure defining a plane, the liquid sample receiving interface being configured to receive a liquid sample; and
   at least one testing strip fluidly connected to the liquid sample receiving interface, a testing strip of the at least one testing strip having, in a planar state, a testing strip center line length, a testing strip width and a testing strip thickness that is shorter than the testing strip center line length and the testing strip width, the testing strip comprising:
    a capillary wick fluidly connected to the liquid sample receiving interface and including a test portion, the test portion comprising a respective reacting material configured to react in a predetermined manner to at least one respective pre-specified analyte;
 wherein a width direction of the testing strip extends at an angle smaller than 90° with respect to a normal of the plane defined by the support structure;
 wherein the testing strip is curved, resulting in a shortest distance between two opposite longitudinal ends of a testing strip center line being shorter than the testing strip center line length in the planar state, wherein the liquid sample providing module is configured to be connected to the testing unit at the liquid sample receiving interface that in turn is fluidly connected to the testing strip; and
 wherein the at least one testing strip is a plurality of testing strips, each testing strip being fluidly connected to the liquid sample receiving interface.

24. The testing device of claim 23, wherein the liquid sample providing module comprises at least one of a needle, a catheter, a cannula or a lancet extending outwardly from the support structure.

25. The testing device of claim 23, wherein the testing strip is fully enclosed within the support structure and the cover unit.

26. A testing device for lateral flow assay, the testing device comprising:
 a testing unit for lateral flow assay; and
 a liquid sample providing module configured to be connected to the testing unit, the testing unit comprising:
  a testing assembly for lateral flow assay; and
  a cover unit attachable to a support structure, the testing assembly comprising:
   a liquid sample receiving interface arranged on the support structure defining a plane, the liquid sample receiving interface being configured to receive a liquid sample; and
   at least one testing strip fluidly connected to the liquid sample receiving interface, a testing strip of the at least one testing strip having, in a planar state, a testing strip center line length, a testing strip width and a testing strip thickness that is shorter than the testing strip center line length and the testing strip width, the testing strip comprising:
    a capillary wick fluidly connected to the liquid sample receiving interface and including a test portion, the test portion comprising a respective reacting material configured to react in a predetermined manner to at least one respective pre-specified analyte;
 wherein a width direction of the testing strip extends at an angle smaller than 90° with respect to a normal of the plane defined by the support structure, wherein the testing strip is fully enclosed within the support structure and the cover unit; and
 wherein the testing strip is curved, resulting in a shortest distance between two opposite longitudinal ends of a testing strip center line being shorter than the testing strip center line length in the planar state, wherein the liquid sample providing module is configured to be connected to the testing unit at the liquid sample receiving interface that in turn is fluidly connected to the testing strip.

* * * * *